(12) United States Patent
Karavany et al.

(10) Patent No.: US 11,865,023 B2
(45) Date of Patent: *Jan. 9, 2024

(54) AORTIC PRESSURE LOSS REDUCTION APPARATUS AND METHODS

(71) Applicant: HEMODYNAMX-TECHNOLOGIES LTD., Modiin (IL)

(72) Inventors: Sagy Karavany, Kibbutz Dvir (IL); Menashe Yacoby, Shoham (IL); Tanhum Feld, Moshav Merhavya (IL)

(73) Assignee: HEMODYNAMX-TECHNOLOGIES LTD., Modin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/526,053

(22) Filed: Nov. 15, 2021

(65) Prior Publication Data

US 2022/0071788 A1  Mar. 10, 2022

Related U.S. Application Data

(63) Continuation of application No. 16/763,884, filed as application No. PCT/IB2018/058961 on Nov. 14, 2018, now Pat. No. 11,207,200.

(Continued)

(51) Int. Cl.
*A61F 2/07* (2013.01)
*A61F 2/966* (2013.01)
(Continued)

(52) U.S. Cl.
CPC ............ *A61F 2/9662* (2020.05); *A61F 2/07* (2013.01); *A61F 2/848* (2013.01); *A61F 2/915* (2013.01);
(Continued)

(58) Field of Classification Search
CPC .......... A61F 2/07; A61F 2/915; A61F 2/9662; A61F 2/848; A61F 2002/068;
(Continued)

(56) References Cited

U.S. PATENT DOCUMENTS

| 5,139,515 A | 8/1992 | Robicsek |
| 6,120,534 A | 9/2000 | Ruiz |

(Continued)

FOREIGN PATENT DOCUMENTS

| CN | 101287424 A | 10/2008 |
| EP | 1849440 A1 | 10/2007 |

(Continued)

OTHER PUBLICATIONS

Communication Pursuant to Article 94(3) EPC for European Patent Application No. 16748842.8 dated Jun. 17, 2022.

(Continued)

*Primary Examiner* — Dinah Baria
(74) *Attorney, Agent, or Firm* — Dorsey & Whitney LLP

(57) ABSTRACT

Apparatus and methods are described including implanting an aortic pressure-loss-reduction device in a subject's ascending aorta. While the device is inside a catheter, a distal end of the catheter is placed within the ascending aorta. A proximal covering sheath of the catheter is retracted such as to uncover at least a portion of a downstream anchor, such that the uncovered portion of the downstream anchor includes a portion of the frame that does not have material coupled thereto. Subsequently, a distal covering sheath of the catheter is advanced, such as to cause an upstream anchor to anchor an upstream end device to the subject's ascending aorta, by the upstream anchor radially expanding against an inner wall of the ascending aorta. Other applications are also described.

20 Claims, 18 Drawing Sheets

Related U.S. Application Data

(60) Provisional application No. 62/630,406, filed on Feb. 14, 2018, provisional application No. 62/586,258, filed on Nov. 15, 2017.

(51) Int. Cl.
    *A61F 2/848* (2013.01)
    *A61F 2/915* (2013.01)
    *A61F 2/06* (2013.01)

(52) U.S. Cl.
    CPC . *A61F 2002/068* (2013.01); *A61F 2002/8486* (2013.01); *A61F 2002/91541* (2013.01); *A61F 2230/0067* (2013.01)

(58) Field of Classification Search
    CPC .... A61F 2002/91541; A61F 2002/8486; A61F 2230/0067
    See application file for complete search history.

(56) References Cited

U.S. PATENT DOCUMENTS

| | | |
|---|---|---|
| 7,018,404 B2 | 3/2006 | Holmberg et al. |
| 7,766,814 B2 | 8/2010 | Walsh |
| 8,585,572 B2 | 11/2013 | Mehmanesh |
| 8,623,065 B2 | 1/2014 | Lau et al. |
| 8,715,337 B2 | 5/2014 | Chuter |
| 9,232,992 B2 | 1/2016 | Heidner et al. |
| 10,368,985 B2 | 8/2019 | Wilson et al. |
| 10,568,731 B2 | 2/2020 | Karavany et al. |
| 11,207,200 B2 | 12/2021 | Karavany et al. |
| 11,224,503 B2 | 1/2022 | Karavany et al. |
| 2003/0045828 A1 | 3/2003 | Wilk |
| 2004/0093058 A1 | 5/2004 | Cottone et al. |
| 2004/0249439 A1 | 12/2004 | Richter et al. |
| 2004/0260389 A1 | 12/2004 | Case et al. |
| 2005/0222674 A1 | 10/2005 | Paine |
| 2006/0009835 A1 | 1/2006 | Osborne et al. |
| 2006/0106449 A1 | 5/2006 | Ben |
| 2006/0149360 A1 | 7/2006 | Schwammenthal et al. |
| 2006/0259134 A1 | 11/2006 | Schwammenthal et al. |
| 2007/0185565 A1 | 8/2007 | Schwammenthal et al. |
| 2007/0293808 A1 | 12/2007 | Williams et al. |
| 2008/0071361 A1 | 3/2008 | Tuval et al. |
| 2008/0071363 A1 | 3/2008 | Tuval et al. |
| 2009/0105805 A1 | 4/2009 | Baker et al. |
| 2009/0198315 A1 | 8/2009 | Boudjemline |
| 2009/0210047 A1 | 8/2009 | Amplatz et al. |
| 2009/0222078 A1 | 9/2009 | Greenberg |
| 2009/0240320 A1 | 9/2009 | Tuval et al. |
| 2009/0270965 A1 | 10/2009 | Sinha et al. |
| 2010/0023046 A1 | 1/2010 | Heidner et al. |
| 2010/0145433 A1 | 6/2010 | Anukhin et al. |
| 2011/0288634 A1 | 11/2011 | Tuval et al. |
| 2012/0010690 A1 | 1/2012 | Richter et al. |
| 2012/0022629 A1 | 1/2012 | Perera et al. |
| 2013/0013053 A1 | 1/2013 | Hartley et al. |
| 2013/0144383 A1 | 6/2013 | Thill et al. |
| 2013/0178750 A1 | 7/2013 | Sheehan et al. |
| 2014/0257474 A1 | 9/2014 | Roeder |
| 2015/0238315 A1 | 8/2015 | Rabito et al. |
| 2015/0366693 A1 | 12/2015 | Kagan et al. |
| 2017/0042551 A1 | 2/2017 | Celermajer et al. |
| 2018/0036109 A1 | 2/2018 | Karavany et al. |
| 2018/0353281 A1 | 12/2018 | Nussinovitch |
| 2019/0183629 A1 | 6/2019 | Karavany et al. |
| 2021/0169634 A1 | 6/2021 | Karavany et al. |

FOREIGN PATENT DOCUMENTS

| | | |
|---|---|---|
| EP | 2016961 B1 | 2/2010 |
| EP | 2777618 A1 | 9/2014 |
| EP | 2896387 A1 | 7/2015 |
| EP | 2785277 B1 | 4/2017 |
| JP | 2001527453 A | 12/2001 |
| JP | 2007526789 A | 9/2007 |
| JP | 2008537891 A | 10/2008 |
| JP | 2011502628 A | 1/2011 |
| WO | 9852476 A1 | 11/1998 |
| WO | 03028522 A2 | 4/2003 |
| WO | 2005002466 A2 | 1/2005 |
| WO | 2005084730 A1 | 9/2005 |
| WO | 2006070372 A2 | 7/2006 |
| WO | 2006080010 A2 | 8/2006 |
| WO | 2009061419 A1 | 5/2009 |
| WO | 2012018590 A1 | 2/2012 |
| WO | 2015013344 A2 | 1/2015 |
| WO | 2016128983 A1 | 8/2016 |
| WO | 2018029688 A1 | 2/2018 |
| WO | 2018220589 A1 | 12/2018 |
| WO | 2019097424 A2 | 5/2019 |
| WO | 2020234787 A1 | 11/2020 |

OTHER PUBLICATIONS

Examination Report for European Application No. 16748842.8 dated Jun. 17, 2022.
First Action Interview Pilot Program Pre-Interview Communication for U.S. Appl. No. 16/743,721 dated Dec. 3, 2021.
Issue Notification for U.S. Appl. No. 16/322,047 dated Dec. 28, 2021.
Issue Notification for U.S. Appl. No. 16/763,884 dated Dec. 8, 2021.
Issue Notification for U.S. Appl. No. 16/743,721 dated May 25, 2022.
Notice of Allowance for U.S. Appl. No. 16/743,721 dated Feb. 22, 2022.
U.S. Appl. No. 62/850,656, filed May 21, 2019.
European Search Report for European Application No. 16748842.8 dated Sep. 19, 2018.
Examination Report for Indian Application No. 201717029373 dated Oct. 8, 2020.
Extended European Search Report for European Application No. 18878693.3 dated Jul. 8, 2021.
Final Office Action for U.S. Appl. No. 15/550,661 dated Jun. 19, 2019.
International Search Report and Written Opinion from International Application No. PCT/IB2018/058961 dated May 8, 2019.
International Search Report and Written Opinion from International Application No. PCT/IB2020/054761 dated Aug. 18, 2020.
International Search Report and Written Opinion from International Application No. PCT/IL2016/050170 dated Jun. 10, 2016.
International Search Report and Written Opinion from International Application No. PCT/IL2017/050884 dated Oct. 30, 2017.
Issue Notification for U.S. Appl. No. 15/550,661 dated Feb. 5, 2020.
Non-Final Office Action for U.S. Appl. No. 15/550,661 dated Aug. 6, 2019.
Non-Final Office Action for U.S. Appl. No. 15/550,661 dated Feb. 20, 2019.
Non-Final Office Action for U.S. Appl. No. 16/322,047 dated Mar. 3, 2021.
Notice of Allowance for U.S. Appl. No. 15/550,661 dated Oct. 17, 2019.
Notice of Allowance for U.S. Appl. No. 16/322,047 dated Sep. 14, 2021.
Notice of Allowance for U.S. Appl. No. 16/763,884 dated Aug. 16, 2021.
Office Action for Chinese Application No. 201680015323.5 dated Dec. 14, 2018.
Office Action for Chinese Application No. 201780049360.2 dated May 25, 2021.
Office Action for Chinese Application No. 201780049360.2 dated Oct. 10, 2020.
Office Action for Chinese Application No. 201910988467.4 dated May 24, 2021.
Office Action for Japanese Application No. 2017-542883 dated Dec. 10, 2019.
Protege webpage—downloaded Mar. 19, 2015.

(56) References Cited

OTHER PUBLICATIONS

Restriction Requirement for U.S. Appl. No. 15/550,661 dated Dec. 4, 2018.
Restriction Requirement for U.S. Appl. No. 16/743,721 dated Sep. 1, 2021.
Supplemental Notice of Allowability for U.S. Appl. No. 15/550,661 dated Jan. 23, 2020.
U.S. Appl. No. 15/550,661, filed Aug. 11, 2017.
U.S. Appl. No. 16/322,047, filed Jan. 30, 2019.
U.S. Appl. No. 16/743,721, filed Jan. 15, 2020.
U.S. Appl. No. 16/763,884, filed May 13, 2020.
U.S. Appl. No. 62/115,207, filed Feb. 12, 2015.
U.S. Appl. No. 62/265,571, filed Dec. 10, 2015.
U.S. Appl. No. 62/373,993, filed Aug. 12, 2016.
U.S. Appl. No. 62/586,258, filed Nov. 15, 2017.
U.S. Appl. No. 62/630,406, filed Feb. 14, 2018.
Heinrich, et al., "Experimental analysis of fluid mechanical energy losses in aortic valve stenosis: importance of pressure recovery", Annals of biomedical engineering, 1996, pp. 685-694.
Examination Report for European Application No. 17755260.1 dated Jun. 1, 2023.
Office Action for Chinese Application No. 201880086395.8 dated Jan. 18, 2023.

AORTIC PRESSURE LOSS REDUCTION APPARATUS AND METHODS

CROSS-REFERENCE TO RELATED APPLICATIONS

The present application is a continuation of U.S. application Ser. No. 16/763,884 to Karavany (published as US 2021/0169634), which is the U.S. national phase of International application No. PCT/IB2018/058961 to Karavany (published as WO 19/097424), filed Nov. 14, 2018, claims priority from:
U.S. Provisional Application No. 62/586,258 to Karavany, filed Nov. 15, 2017, entitled "Aortic implant;" and
U.S. Provisional Application No. 62/630,406 to Karavany, filed Feb. 14, 2018, entitled "Aortic implant."
Both of the above-referenced applications are incorporated herein by reference.

FIELD OF EMBODIMENTS OF THE INVENTION

Some applications of the present invention generally relate to medical apparatus. Specifically, some applications of the present invention relate to an aortic pressure-loss-reduction device and methods of use thereof.

BACKGROUND

Aortic valve stenosis is a common disease in which calcification of the cusps of the aortic valve cause the flexibility of the valve to be compromised and the open valve area to diminish. Once aortic valve stenosis develops, due to the reduction in the aortic valve diameter, blood flow is compromised. Aortic valve stenosis often progresses to heart failure and other life-threatening conditions.

SUMMARY OF EMBODIMENTS

In accordance with some applications of the present invention, an aortic pressure-loss-reduction device is implanted in a subject's ascending aorta. The device typically includes a frame and a material that is configured to impede blood flow therethrough coupled to at least a portion of the frame. While the device is inside a catheter, the distal end of the catheter is typically placed within the subject's ascending aorta. Further typically, the distal end of the catheter is placed in close proximity to the subject's aortic valve (e.g., distally to the subject's sinotubular junction). The device is disposed within the catheter such that the device is maintained in a radially-constrained configuration, and such that an upstream anchor of the device is disposed distally within the catheter with respect to a downstream anchor of the device. A proximal covering sheath of the catheter is retracted, such as to (a) uncover an intermediate portion of the device to allow the intermediate portion to at least partially assume its non-constrained configuration, the intermediate portion of the device defining a conduit, and (b) uncover at least a portion of the downstream anchor, such that the uncovered portion of the downstream anchor includes a portion of the frame that does not have the material coupled to it. Typically, uncovering the portion of the downstream anchor that does not have the material coupled to it facilitates blood flow through the device by allowing blood to flow through the portion of the downstream anchor that does not have the material coupled to it. Subsequently, a distal covering sheath of the catheter is advanced, such as to cause the upstream anchor to anchor an upstream end of the device to the subject's ascending aorta, by the upstream anchor radially expanding against an inner wall of the ascending aorta. Further subsequently, the proximal covering sheath of the catheter is further retracted, such as to cause the downstream anchor to anchor a downstream end of the device to the subject's ascending aorta, by the downstream anchor radially expanding against an inner wall of the ascending aorta.

Typically, in the non-constrained configuration of the device, the frame defines (a) an upstream anchor portion configured to radially expand against the inner wall of the ascending aorta, such as to anchor an upstream end of the aortic pressure-loss-reduction device to the subject's ascending aorta, (b) an intermediate portion that defines a conduit therethrough, such that blood is configured to flow through the device via the conduit, at least a portion of the conduit diverging, such that a downstream end of the diverging portion has a greater cross-sectional area than an upstream end of the diverging portion, and (c) a downstream anchor portion configured to radially expand against the inner wall of the ascending aorta, such as to anchor the downstream end of the aortic pressure-loss-reduction device to the subject's ascending aorta.

Typically, a first set of sinusoidal struts is disposed between the downstream end of the upstream anchor and the upstream end of the intermediate portion, the sinusoidal struts forming a folded portion between the downstream end of the upstream anchor and the upstream end of the intermediate portion. Further typically, a second set of sinusoidal struts is disposed between an upstream end of the downstream anchor and a downstream end of the intermediate portion, the sinusoidal struts forming a folded portion between the upstream end of the downstream anchor and the downstream end of the intermediate portion. For some applications, the aortic pressure-loss-reduction device is configured, such that the intermediate portion of the device is (a) longitudinally fixed with respect to the ascending aorta by the upstream anchor portion and the downstream anchor portion exerting radial force against the inner wall of the aorta and (b) able to adjust the angle that a longitudinal axis of the intermediate portion makes with longitudinal axes of the upstream and downstream anchor portions, by the folded portions acting as hinges about which the intermediate portion can flex. For some applications, the aortic pressure-loss-reduction device is configured such that, by virtue of a flexibility of the folded portions, a length of the intermediate portion does not change even if a distance between the upstream and downstream anchor portions changes.

For some applications, an upstream end of the intermediate portion is reinforced with respect to at least a central portion of the intermediate portion, such that in response to the diameter of the upstream anchor changing by an absolute amount, an absolute change in the diameter of the upstream end of the intermediate portion is less than the absolute amount by which the diameter of the upstream anchor changed. For example, a ratio of the absolute change in the diameter of the upstream end of the intermediate portion to the absolute amount by which the diameter of the upstream anchor changed may be less than 1:2. For some applications, the upstream end of the intermediate portion is reinforced with respect to at least a central portion of the intermediate portion by struts of the upstream end of the intermediate portion forming closed cells. Alternatively or additionally, the upstream end of the intermediate portion is reinforced with respect to at least a central portion of the intermediate portion by the struts of the upstream end being shorter than the struts of the central portion of the intermediate portion, and/or being wider than the struts of the central portion of the intermediate portion. For some applications, the sinusoidal struts belonging to the first set of sinusoidal struts are configured to have a flexibility that is such that in response to the diameter of the upstream anchor changing, the sinusoidal struts belonging to the first set of sinusoidal struts absorb at least some of the change in the diameter.

Typically, the intermediate portion of the frame is configured to be flexible, such that at least upon the aortic pressure-loss-reduction device being implanted inside the subject's ascending aorta, the intermediate portion of the frame curves such as to conform with a curvature of the ascending aorta. For example, the frame may be configured to be flexible, by the intermediate portion of the frame including gaps between rows of struts, the rows of struts being connected to each other via the material. Alternatively or additionally, the intermediate portion of the frame is configured to be flexible, by the intermediate portion of the frame including struts that form a spiral. Further alternatively or additionally, the intermediate portion of the frame may be configured to be flexible, by the intermediate portion of the frame including alternating rows of struts, widths of the struts in a second set of the alternating rows of struts being less than widths of the struts in a first set of the alternating rows of struts, and/or a density of the struts in a second set of the alternating rows of struts being less than the density of the struts in a first set of the alternating rows of struts.

There is therefore provided, in accordance with some applications of the present invention, a method including:
implanting an aortic pressure-loss-reduction device in an ascending aorta of a subject, the aortic pressure-loss-reduction device including a frame and a material that is configured to impede blood flow therethrough coupled to at least a portion of the frame, by, sequentially:
while the aortic pressure-loss-reduction device is inside a catheter, placing a distal end of the catheter within the subject's ascending aorta, the aortic pressure-loss-reduction device being disposed within the catheter such the device is maintained in a radially-constrained configuration and such that an upstream anchor of the device is disposed distally within the catheter with respect to a downstream anchor of the device;
retracting a proximal covering sheath of the catheter, such as to:
uncover an intermediate portion of the aortic pressure-loss-reduction device to allow the intermediate portion to at least partially assume its non-constrained configuration, the intermediate portion of the device being configured to define a conduit through the device; and
uncover at least a portion of the downstream anchor, such that the uncovered portion of the downstream anchor includes a portion of the frame that does not have the material coupled thereto;
advancing a distal covering sheath of the catheter, such as to cause the upstream anchor to anchor an upstream end of the aortic pressure-loss-reduction device to the subject's ascending aorta, by the upstream anchor radially expanding against an inner wall of the ascending aorta; and
further retracting the proximal covering sheath of the catheter, such as to cause the downstream anchor to anchor a downstream end of the aortic pressure-loss-reduction device to the subject's ascending aorta, by the downstream anchor radially expanding against an inner wall of the ascending aorta.

For some applications, the method further includes, while retracting the proximal covering sheath of the catheter, preventing the upstream anchor from radially expanding by holding projections that protrude from an upstream end of the upstream anchor within the distal covering sheath of the catheter.

For some applications, retracting the proximal covering sheath of the catheter such as to uncover the portion of the downstream anchor that does not have the material coupled to it includes facilitating blood flow through the device by allowing blood to flow through the portion of the downstream anchor that does not have the material coupled thereto.

For some applications, causing the downstream anchor to anchor a downstream end of the device to the subject's ascending aorta, by the downstream anchor radially expanding against an inner wall of the ascending aorta includes preventing blood flow to a brachiocephalic artery of the subject being occluded by deploying the downstream anchor such that the portion of the frame that does not have the material coupled to it is deployed closest to the brachiocephalic artery.

For some applications:
while the device is inside the catheter at least a portion of the device is disposed around a conically-shaped mount portion that converges toward a proximal end of the catheter, and
the method further includes, subsequent to further retracting the proximal covering sheath of the catheter such as to cause the downstream anchor to anchor a downstream end of the device to the subject's ascending aorta, retracting the mount portion through the conduit, the conical shape of the mount portion being configured to facilitate retraction of the mount through the conduit.

For some applications, implanting the aortic pressure-loss-reduction device in the subject's ascending aorta includes implanting the aortic pressure-loss-reduction device in the subject's ascending aorta such that an upstream end of the conduit is disposed within 25 mm of an aortic valve orifice of the subject. For some applications, advancing the distal covering sheath of the catheter, such as to cause the upstream anchor to anchor the upstream end of the device to the subject's ascending aorta, by the upstream anchor radially expanding against an inner wall of the ascending aorta includes causing the upstream end of the upstream anchor to become deployed within 5 mm of a sinotubular junction of the subject. For some applications, causing the upstream end of the upstream anchor to become deployed within 5 mm of the subject's sinotubular junction includes causing the upstream end of the upstream anchor to become deployed within 5 mm of the subject's sinotubular junction, upstream of the subject's sinotubular junction. For some applications, causing the upstream end of the upstream anchor to become deployed within 5 mm of the subject's sinotubular junction includes causing the upstream end of the upstream anchor to become deployed within 5 mm of the subject's sinotubular junction, downstream of the subject's sinotubular junction.

There is further provided, in accordance with some applications of the present invention, apparatus including:
an aortic pressure-loss-reduction device configured to be implanted in an ascending aorta of a subject, the aortic pressure-loss-reduction device including a frame, and a material that is configured to impede blood flow therethrough coupled to at least a portion of the frame, the aortic pressure-loss-reduction device being configured such that in a non-radially-constrained configuration of the device, the device defines:
an upstream anchor,
a downstream anchor, at least a portion of the downstream anchor being defined by the frame and not including any material coupled to the frame, and
an intermediate portion of the device that defines a conduit through the aortic pressure-loss-reduction device; and
a catheter configured to be inserted into the subject's ascending aorta, while housing the aortic pressure-loss-reduction device inside the catheter in a radially constrained configuration, with the upstream anchor disposed within the catheter distally with respect to the downstream anchor, the catheter including:
a proximal covering sheath configured to be retracted such as to:
uncover the intermediate portion of the aortic pressure-loss-reduction device to allow the intermediate portion to at least partially assume its non-constrained configuration, and
uncover at least a portion of the downstream anchor, such that the uncovered portion of the downstream anchor includes the portion of the frame that does not have the material coupled thereto;
a distal covering sheath of the catheter configured, subsequent to the proximal covering sheath being retracted such as to uncover at least the portion of the downstream anchor, to be advanced distally as to cause the upstream anchor to anchor an upstream end of the aortic pressure-loss-reduction device to the subject's ascending aorta, by the upstream anchor radially expanding against an inner wall of the ascending aorta,
the proximal covering sheath being further configured, subsequent to the distal covering sheath being advanced distally, to be further retracted, such as to cause the downstream anchor to anchor a downstream end of the aortic pressure-loss-reduction device to the subject's ascending aorta, by the downstream anchor radially expanding against the inner wall of the ascending aorta.

For some applications, the catheter further includes a mount, at least a distal portion of which defines a conical shape that converges toward a proximal end of the catheter, the distal portion of the mount being configured such that:
while the device is inside the catheter at least a portion of the device is disposed around the distal portion of the mount, and
the conical shape of the distal portion of the mount is configured to facilitate retraction of the distal portion of the mount through the conduit.

For some applications, the aortic pressure-loss-reduction device is configured to be implanted in the subject's ascending aorta such that an upstream end of the conduit is disposed within 25 mm of an aortic valve orifice of the subject. For some applications, the aortic pressure-loss-reduction device is configured to be implanted in the subject's ascending aorta such that an upstream end of the upstream anchor is deployed within 5 mm of a sinotubular junction of the subject. For some applications, the aortic pressure-loss-reduction device is configured to be implanted in the subject's ascending aorta such that the upstream end of the upstream anchor is deployed within 5 mm of the subject's sinotubular junction, upstream of the subject's sinotubular junction. For some applications, the aortic pressure-sure-loss-reduction device is configured to be implanted in the subject's ascending aorta such that the upstream end of the upstream anchor is deployed within 5 mm of the subject's sinotubular junction, downstream of the subject's sinotubular junction.

For some applications, the aortic pressure-loss-reduction device further includes a plurality of projections that protrude from an upstream end of the upstream anchor, and the distal covering sheath of the catheter is configured to prevent the upstream anchor from radially expanding by holding the projections. For some applications, the projections includes T-shaped projections. For some applications, the projections each have lengths of less than 8 mm. For some applications, upstream ends of the projections are curved such as to be atraumatic.

There is further provided, in accordance with some applications of the present invention, apparatus including:
an aortic pressure-loss-reduction device configured to be implanted inside an ascending aorta of a subject, the aortic pressure-loss-reduction device including:
a frame that is configured, in a non-constrained configuration thereof, to define:
an upstream anchor portion configured to radially expand against an inner wall of a subject's ascending aorta, such as to anchor an upstream end of the aortic pressure-loss-reduction device to the subject's ascending aorta;
an intermediate portion configured to define a conduit therethrough, such that blood is configured to flow through the device via the conduit, at least a portion of the conduit diverging, such that a downstream end of the diverging portion has a greater cross-sectional area than an upstream end of the diverging portion, and at least a portion of the intermediate portion including struts that form a spiral along the intermediate portion;
a downstream anchor portion configured to radially expand against an inner wall of a subject's ascending aorta, such as to anchor a downstream end of the aortic pressure-loss-reduction device to the subject's ascending aorta;
a first set of sinusoidal struts disposed between a downstream end of the upstream anchor and an upstream end of the intermediate portion, the sinusoidal struts being shaped to form a folded portion between the downstream end of the upstream anchor and the upstream end of the intermediate portion; and
a second set of sinusoidal struts disposed between an upstream end of the downstream anchor and a downstream end of the intermediate portion, the sinusoidal struts being shaped to form a folded portion between the upstream end of the downstream anchor and the downstream end of the intermediate portion; and
a material layer coupled to the frame, the material layer configured to impede blood flow therethrough.

For some applications, the struts that form the spiral along the intermediate portion are configured such that at least upon the aortic pressure-loss-reduction device being implanted inside the subject's ascending aorta, the intermediate portion of the frame curves such as to conform with a curvature of the ascending aorta.

For some applications, the upstream anchor portion includes a flared skirt at an upstream end of the upstream anchor portion, the flared skirt being configured to become deployed within aortic sinuses of the subject. For some applications, the upstream anchor portion includes a plurality of anchors at an upstream end of the upstream anchor portion, the anchors being configured to become deployed within respective aortic sinuses of the subject. For some applications, the intermediate portion includes one or more centralizing anchors extending radially therefrom, the centralizing anchors being configured to at least partially centralize the conduit with respect to a longitudinal axis of the aorta.

For some applications, at least at a downstream portion of the downstream anchor portion, the frame does not include the material layer coupled thereto. For some applications, the material layer is coupled to an outside of at least a portion of the frame. For some applications, the material layer is coupled to an inside of at least a portion of the frame. For some applications, at least a portion of the frame is embedded within the material layer.

For some applications, the sinusoidal struts belonging to the first set of sinusoidal struts are longer than the sinusoidal struts belonging to the second set of sinusoidal struts. For some applications, the first set of sinusoidal struts is configured such that a distance from an upstream end of the upstream anchor to an upstream end of the conduit is less than 15 mm. For some applications, the first set of sinusoidal struts is configured such that an upstream end of the conduit extends beyond an upstream end of the upstream anchor in the upstream direction.

For some applications, the aortic pressure-loss-reduction device is configured, such that the intermediate portion of the device is (a) longitudinally fixed with respect to the ascending aorta by the upstream anchor portion and the downstream anchor portion exerting radial force against the inner wall of the ascending aorta and (b) able to adjust the angle that a longitudinal axis of the intermediate portion makes with longitudinal axes of the upstream and downstream anchor portions, by the folded portions acting as hinges about which the intermediate portion can flex. For some applications, the aortic pressure-loss-reduction device is configured such that, by virtue of a flexibility of the folded portions, a length of the intermediate portion does not change even if a distance between the upstream and downstream anchor portions changes.

For some applications, the aortic pressure-loss-reduction device is configured such that in response to a diameter of the upstream anchor changing by a given absolute amount, a diameter of an upstream end of the conduit does not change by the given absolute amount.

For some applications, an upstream end of the intermediate portion is reinforced with respect to at least a longitudinally-central portion of the intermediate portion, such that in response to a diameter of the upstream anchor changing by an absolute amount, an absolute change in a diameter of the upstream end of the intermediate portion is less than the absolute amount by which the diameter of the upstream anchor changed. For some applications, the upstream end of the intermediate portion is reinforced with respect to at least the longitudinally-central portion of the intermediate portion, such that a ratio of the absolute change in a diameter of the upstream end of the intermediate portion to the absolute amount by which the diameter of the upstream anchor changes is less than 1:2. For some applications, the upstream end of the intermediate portion includes struts, and the upstream end of the intermediate portion is reinforced with respect to at least the longitudinally-central portion of the intermediate portion by the struts of the upstream end of the intermediate portion forming closed cells. For some applications, the upstream end of the intermediate portion and the longitudinally-central portion of the intermediate portion include struts, and the upstream end of the intermediate portion is reinforced with respect to at least the longitudinally-central portion of the intermediate portion by the struts of the upstream end being shorter than the struts of the longitudinally-central portion of the intermediate portion. For some applications, the upstream end of the intermediate portion and the longitudinally-central portion of the intermediate portion include struts, and the upstream end of the intermediate portion is reinforced with respect to at least the longitudinally-central portion of the intermediate portion by the struts of the upstream end being wider than the struts of the longitudinally-central portion of the intermediate portion.

For some applications, the sinusoidal struts belonging to the first set of sinusoidal struts are configured to have a flexibility that is such that in response to a diameter of the upstream anchor changing by an absolute amount, an absolute change in a diameter of the upstream end of the intermediate portion is less than the absolute amount by which the diameter of the upstream anchor changed. For some applications, the flexibility of the sinusoidal struts belonging to the first set of sinusoidal struts is such that a ratio of the absolute change in a diameter of the upstream end of the intermediate portion to the absolute amount by which the diameter of the upstream anchor changes is less than 1:2.

For some applications, the aortic pressure-loss-reduction device further includes a plurality of projections from an upstream end of the upstream anchor portion, the projections being configured to facilitate holding the upstream anchor portion in a radially-constrained configuration, even when the intermediate portion is at least partially in a non-radially-constrained configuration. For some applications, the projections includes T-shaped projections. For some applications, the projections each have lengths of less than 8 mm. For some applications, upstream ends of the projections are curved such as to be atraumatic.

There is further provided, in accordance with some applications of the present invention, a method including:
  placing an aortic pressure-loss-reduction device inside an ascending aorta of a subject, the aortic pressure-loss-reduction device including a frame and a material layer coupled to an inside of at least a portion of the frame, the material being configured to impede blood flow therethrough; and
  deploying the aortic pressure-loss-reduction device inside the ascending aorta, such that the frame of the aortic pressure-loss-reduction defines:
    an upstream anchor portion that radially expands against an inner wall of a subject's ascending aorta, such as to anchor an upstream end of the aortic pressure-loss-reduction device to the subject's ascending aorta;
    an intermediate portion that defines a conduit therethrough, such that blood flows through the device via the conduit, at least a portion of the conduit diverging, such that a downstream end of the diverging portion has a greater cross-sectional area than an upstream end of the diverging portion, and at least a portion of the intermediate portion including struts that form a spiral along the intermediate portion;
    a downstream anchor portion that radially expands against an inner wall of a subject's ascending aorta, such as to anchor a downstream end of the aortic pressure-loss-reduction device to the subject's ascending aorta;

a first set of sinusoidal struts disposed between a downstream end of the upstream anchor and an upstream end of the intermediate portion, the sinusoidal struts forming a folded portion between the downstream end of the upstream anchor and the upstream end of the intermediate portion; and a second set of sinusoidal struts disposed between an upstream end of the downstream anchor and a downstream end of the intermediate portion, the sinusoidal struts forming a folded portion between the upstream end of the downstream anchor and the downstream end of the intermediate portion.

There is further provided, in accordance with some applications of the present invention, apparatus including:

an aortic pressure-loss-reduction device configured to be implanted inside an ascending aorta of a subject, the aortic pressure-loss-reduction device including:

a frame that is configured, in a non-constrained configuration thereof, to define:

an upstream anchor portion configured to radially expand against an inner wall of a subject's ascending aorta, such as to anchor an upstream end of the aortic pressure-loss-reduction device to the subject's ascending aorta;

an intermediate portion configured to define a conduit therethrough, such that blood is configured to flow through the device via the conduit, at least a portion of the conduit diverging, such that a downstream end of the diverging portion has a greater cross-sectional area than an upstream end of the diverging portion;

a downstream anchor portion configured to radially expand against an inner wall of a subject's ascending aorta, such as to anchor a downstream end of the aortic pressure-loss-reduction device to the subject's ascending aorta;

a first set of sinusoidal struts disposed between a downstream end of the upstream anchor and an upstream end of the intermediate portion, the sinusoidal struts being shaped to form a folded portion between the downstream end of the upstream anchor and the upstream end of the intermediate portion;

an upstream end of the intermediate portion being reinforced with respect to at least a longitudinally-central portion of the intermediate portion, such that in response to a diameter of the upstream anchor changing by an absolute amount, an absolute change in a diameter of the upstream end of the intermediate portion is less than the absolute amount by which the diameter of the upstream anchor changes; and a material layer coupled to at least a portion of the frame, the material layer configured to impede blood flow therethrough.

For some applications, the frame is non-axisymmetric, such that at least upon the aortic pressure-loss-reduction device being implanted inside the subject's ascending aorta, the intermediate portion of the frame curves such as to conform with a curvature of the ascending aorta. For some applications, the frame is non-axisymmetric, such that at least upon the aortic pressure-loss-reduction device being implanted inside the subject's ascending aorta, the intermediate portion of the frame is disposed at an angle with respect to the upstream anchor portion, such as to conform with a curvature of the ascending aorta.

For some applications, the upstream anchor portion includes a flared skirt at an upstream end of the upstream anchor portion, the flared skirt being configured to become deployed within aortic sinuses of the subject. For some applications, the upstream anchor portion includes a plurality of anchors at an upstream end of the upstream anchor portion, the anchors being configured to become deployed within respective aortic sinuses of the subject. For some applications, the intermediate portion includes one or more centralizing anchors extending radially therefrom, the centralizing anchors being configured to at least partially centralize the conduit with respect to a longitudinal axis of the aorta.

For some applications, at least at a downstream portion of the downstream anchor portion, the frame does not include the material layer coupled thereto. For some applications, the material layer is coupled to an outside of at least a portion of the frame. For some applications, the material layer is coupled to an inside of at least a portion of the frame. For some applications, at least a portion of the frame is embedded within the material layer.

For some applications, the first set of sinusoidal struts is configured such that a distance from an upstream end of the upstream anchor to an upstream end of the conduit is less than 15 mm. For some applications, the first set of sinusoidal struts is configured such that an upstream end of the conduit extends beyond an upstream end of the upstream anchor in the upstream direction.

For some applications, the upstream end of the intermediate portion is reinforced with respect to at least the longitudinally-central portion of the intermediate portion, such that a ratio of the absolute change in a diameter of the upstream end of the intermediate portion to the absolute amount by which the diameter of the upstream anchor changes is less than 1:2.

For some applications, the upstream end of the intermediate portion includes struts, and the upstream end of the intermediate portion is reinforced with respect to at least the longitudinally-central portion of the intermediate portion by the struts of the upstream end of the intermediate portion forming closed cells. For some applications, the upstream end of the intermediate portion and the longitudinally-central portion of the intermediate portion include struts, and the upstream end of the intermediate portion is reinforced with respect to at least the longitudinally-central portion of the intermediate portion by the struts of the upstream end being shorter than the struts of the longitudinally-central portion of the intermediate portion. For some applications, the upstream end of the intermediate portion and the longitudinally-central portion of the intermediate portion include struts, and the upstream end of the intermediate portion is reinforced with respect to at least the longitudinally-central portion of the intermediate portion by the struts of the upstream end being wider than the struts of the longitudinally-central portion of the intermediate portion.

For some applications, the sinusoidal struts belonging to the first set of sinusoidal struts are configured to have a flexibility that is such that in response to the diameter of the upstream anchor changing, the sinusoidal struts belonging to the first set of sinusoidal struts absorb at least some of the change in the diameter.

For some applications, the aortic pressure-loss-reduction device further includes a plurality of projections from an upstream end of the upstream anchor portion, the projections being configured to facilitate holding the upstream anchor portion in a radially-constrained configuration, even when the intermediate portion is at least partially in a non-radiallyconstrained configuration. For some applications, the projections includes T-shaped projections. For some applications, the projections each have lengths of less than 8 mm. For some applications, upstream ends of the projections are curved such as to be atraumatic.

For some applications, the intermediate portion of the frame is configured to be flexible, such that at least upon the aortic pressure-loss-reduction device being implanted inside the subject's ascending aorta, the intermediate portion of the frame curves such as to conform with a curvature of the ascending aorta. For some applications, the intermediate portion of the frame is configured to be flexible, by the intermediate portion of the frame including gaps between rows of struts, the rows of struts being connected to each other via the material. For some applications, the intermediate portion of the frame is configured to be flexible, by the intermediate portion of the frame including struts that form a spiral. For some applications, the intermediate portion of the frame is configured to be flexible, by the intermediate portion of the frame including alternating rows of struts, widths of the struts in a second set of the alternating rows of struts being less than widths of the struts in a first set of the alternating rows of struts. For some applications, the intermediate portion of the frame is configured to be flexible, by the intermediate portion of the frame including alternating rows of struts, a density of the struts in a second set of the alternating rows of struts being less than the density of the struts in a first set of the alternating rows of struts. For some applications, struts of the second set of the alternating rows of struts are sinusoidal.

For some applications, the frame further includes a second set of sinusoidal struts disposed between an upstream end of the downstream anchor and a downstream end of the intermediate portion, the sinusoidal struts being shaped to form a folded portion between the upstream end of the downstream anchor and the downstream end of the intermediate portion. For some applications, the aortic pressure-loss-reduction device is configured, such that the intermediate portion of the device is (a) longitudinally fixed with respect to the ascending aorta by the upstream anchor portion and the downstream anchor portion exerting radial force against the inner wall of the aorta and (b) able to adjust the angle that a longitudinal axis of the intermediate portion makes with longitudinal axes of the upstream and downstream anchor portions, by the folded portions acting as hinges about which the intermediate portion can flex. For some applications, the aortic pressure-loss-reduction device is configured such that, by virtue of a flexibility of the folded portions, a length of the intermediate portion does not change even if a distance between the upstream and downstream anchor portions changes. For some applications, the sinusoidal struts belonging to the first set of sinusoidal struts are longer than the sinusoidal struts belonging to the second set of sinusoidal struts.

There is further provided, in accordance with some applications of the present invention, a method including:
placing an aortic pressure-loss-reduction device inside an ascending aorta of a subject, the aortic pressure-loss-reduction device including a frame and a material layer coupled to an inside of at least a portion of the frame, the material being configured to impede blood flow therethrough; and
deploying the aortic pressure-loss-reduction device inside the ascending aorta, such that the frame of the aortic pressure-loss-reduction device defines:
an upstream anchor portion that radially expands against an inner wall of a subject's ascending aorta, such as to anchor an upstream end of the aortic pressure-loss-reduction device to the subject's ascending aorta,
an intermediate portion that defines a conduit therethrough, such that blood flows through the device via the conduit, at least a portion of the conduit diverging, such that a downstream end of the diverging portion has a greater cross-sectional area than an upstream end of the diverging portion,
a downstream anchor portion that radially expands against an inner wall of a subject's ascending aorta, such as to anchor a downstream end of the aortic pressure-loss-reduction device to the subject's ascending aorta,
a first set of sinusoidal struts disposed between a downstream end of the upstream anchor and an upstream end of the intermediate portion, the sinusoidal struts forming a folded portion between the downstream end of the upstream anchor and the upstream end of the intermediate portion, and
an upstream end of the intermediate portion being reinforced with respect to at least a central portion of the intermediate portion, such that in response to a diameter of the upstream anchor changing by an absolute amount, an absolute change in a diameter of the upstream end of the intermediate portion is less than the absolute amount by which the diameter of the upstream anchor changes.

The present invention will be more fully understood from the following detailed description of embodiments thereof, taken together with the drawings, in which:

DETAILED DESCRIPTION OF EMBODIMENTS

Figure 1A:
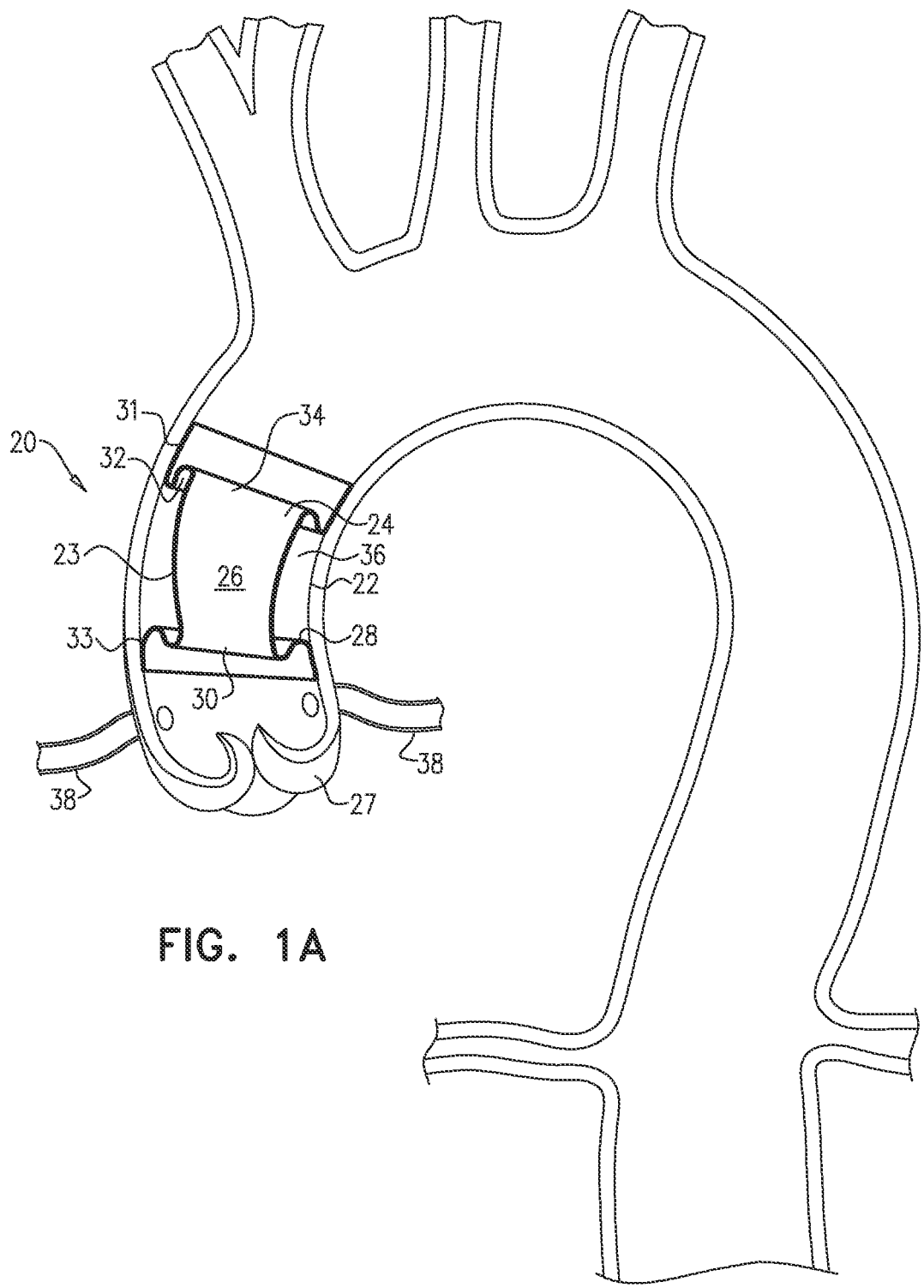
FIGS. 1A and 1B are schematic illustrations of an implantable pressure-loss-reduction device configured to be deployed inside a subject's aorta, in accordance with some applications of the present invention.
Figure 1B:
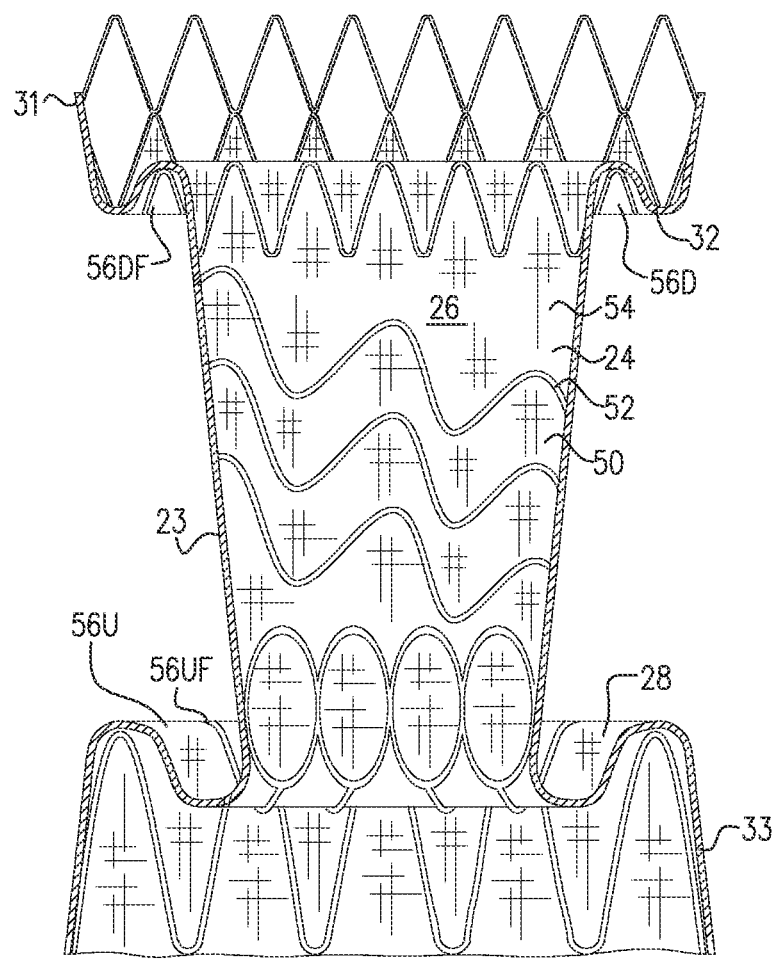

Reference is now made to FIGS. 1A and 1B, which are schematic illustrations of an implantable pressure-loss-reduction device 20 deployed inside a subject's ascending aorta 22, in accordance with some applications of the present invention. FIG. 1A shows the device deployed inside the ascending aorta, and FIG. 1B shows a slice view of the device in a non-constrained configuration (i.e., in the absence of any external force acting upon the device). As shown, device 20 defines an intermediate portion 23 that has an inner surface 24 that defines a conduit 26 through the device, from the upstream end of the device to the downstream end of the device. At least a portion of the conduit diverges in a direction from an upstream end 30 of the conduit to a downstream end 34 of the conduit, such that the cross-sectional area of the conduit at the downstream end is greater than the cross-sectional area of the conduit at the upstream end. In addition, the device is configured such that at least upon being placed inside the subject's ascending aorta, the conduit is curved (i.e., the conduit defines a curved longitudinal axis), such as to conform at least partially to the curvature of the ascending aorta.

Typically, the device is configured such that in its non-constrained configuration at least a portion of the conduit 26 diverges, but the conduit 26 is not curved, as shown in FIG. 1B. For such applications, the intermediate portion of the device is typically configured to be flexible, such that upon being deployed within the ascending aorta, the intermediate portion of the device becomes curved such as to conform at least partially to the curvature of the ascending aorta. For some applications, the device is configured such that even in its non-constrained configuration, at least a portion of conduit 26 diverges, and conduit 26 is also curved. For some applications, the device is configured such that in its non-constrained configuration, a portion of conduit 26 diverges, and is not curved, but rather is disposed at an angle with respect to an upstream anchor 33 of the device (i.e., such that a longitudinal axis of the conduit is disposed at an angle with respect to the longitudinal axis of the upstream anchor), e.g., as described hereinbelow with reference to FIG. 12C.

Pressure-loss-reduction device 20 is typically placed in the ascending aorta of a subject suffering from aortic valve stenosis, in the vicinity of the stenosed aortic valve 27 (e.g., such that the upstream end of the conduit is downstream of the aortic valve, and within 25 mm from the aortic valve tip when the valve is in an open configuration, during systole). The blood exiting the subject's left ventricle, during systole, is directed into conduit 26. The divergence of the conduit is configured to reduce pressure loss of blood flowing through the conduit, relative to the loss of pressure of the blood flowing through the longitudinal portion of the blood vessel in the absence of the device. The conduit reduces the blood pressure loss by reducing the area of flow separation. During diastole, blood flows back toward coronary arteries 38 via conduit 26.

The device is typically deployed within a longitudinal portion of the aorta, such that blood flow through the longitudinal portion of the aorta, via any flow path other than through the conduit, whether in the antegrade or retrograde direction, is less than 20 percent (e.g., less than 10 percent, or less than 5 percent) of the total blood flow through the longitudinal portion of the blood vessel. (In the present application, when used with reference to blood flow, the term "antegrade" refers to blood flowing in the forward directions, and the term "retrograde" refers to blood flowing in a backward direction.) Typically, by directing the blood to flow in the above-described manner, loss of pressure and energy of the blood flow exiting the left ventricle into the ascending aorta is reduced relative to the loss of pressure and energy of the blood flow in the absence of the device. Thus, placement of device 20 in the subject's ascending aorta may decrease the subject's left ventricular pressure, reduce afterload, and/or and improve the subject's cardiac output. For some applications, regulating the blood flow from the aortic valve in the above-described manner may postpone or stop the degradation process leading to further aortic valve stenosis. An unhealthy flow regime in the ascending aorta can cause sequential deposits of thrombi on the valve surface that can cause further valve thickening, deformation and calcification leading to severe stenosis. Device 20, by changing the flow regime, may reduce the inflammatory process that causes the calcification. Thus, device 20 may decrease the degradation of the medical situation of the subject.

It is noted that, typically, device 20 does not include a prosthetic valve disposed within the conduit or at any other location within the device. The device typically performs the functions described herein, without requiring the use of a prosthetic valve of any type.

Typically, the pressure-loss-reduction device includes a downstream anchor 31 at the downstream end of the device that is configured to appose the inner wall of the aorta, and to anchor the downstream end of the device with respect to the aorta by exerting outward radial pressure against the inner wall of the aorta. The device typically defines at least one downstream outer surface 32 that extends from the outside of the conduit to the downstream anchor, which is in contact with the inner wall of the blood vessel. Typically, the at least one surface extends radially outward, around the full circumference of the conduit, from the conduit to the downstream anchor.

Pressure-loss-reduction device 20 typically includes an upstream anchor 33 at the upstream end of the device that is configured to appose the inner wall of the aorta, and to anchor the upstream end of the device with respect to the aorta by exerting outward radial pressure against the inner wall of the aorta. The device typically defines one or more upstream outer surfaces 28 that surround a, upstream portion of conduit 26, and that extend at least from outside the conduit to the upstream anchor. Typically, the at least one upstream outer surface is disposed around the conduit at a longitudinal location such that at least a portion of the upstream surface is within the upstream-most 30 percent (e.g., the upstream-most 20 percent) of the length of the conduit.

Typically, upstream and downstream outer surfaces 28 and 32 are configured such that, when pressure-loss-reduction device 20 is deployed inside a longitudinal portion of the subject's aorta, the surfaces substantially impede blood flow through the longitudinal portion, via any flow path other than through conduit 26. For example, the upstream and downstream surfaces may be configured such that, when the device is deployed inside the longitudinal portion of the subject's aorta, flow via flow paths other than through conduit 26, whether in the antegrade or retrograde direction, is less than 20 percent (e.g., less than 10 percent, or less than 5 percent) of total blood flow through the longitudinal portion of the subject's aorta. Typically, the upstream and downstream surfaces are configured such that, when the device is deployed inside the longitudinal portion of the subject's aorta, there is no blood flow through the longitudinal portion of the subject's aorta via any flow path other than through the conduit defined by the inner surface of the device, whether in the antegrade or retrograde direction. For some applications, each of downstream outer surface 32 and upstream outer surface 28 is configured to impede the backflow of blood around the outside of conduit 26 as well as to impede antegrade blood flow around the outside of conduit 26. For some applications, the device includes a single one of the upstream and downstream outer surfaces, and the single surface is configured to impede both antegrade and retrograde blood flow around the outside of conduit 26.

For some applications (not shown), intermediate portion 23 (which has inner surface 24 that defines conduit 26) is disposed eccentrically with respect to one or both of upstream anchor 33 and downstream anchor 31.

Typically, intermediate portion 23 (which has inner surface 24 that defines conduit 26), as well as upstream anchor 33, downstream anchor 31, and surfaces 28 and 32 are all defined by a single continuous portion of stent graft material 50, that is shaped such as to define the respective components of pressure-loss-reduction device 20, as shown in FIG. 1B. The stent graft material is typically formed from a combination of a metal or alloy frame 52 (e.g., a stent made of stainless steel or nitinol or cobalt chromium) and a covering material 54, e.g., a fabric and/or a polymer (such as expanded polytetrafluoroethylene (ePTFE), or woven, knitted and/or braided polyester), which is typically coupled to the frame via stitching, spray coating, encapsulation, electrospinning, dip molding and/or a different technique. In accordance with some applications, a layer of the material is coupled to the inside of at least a portion of the frame, the outside of at least a portion of the frame, and/or at least a portion of the frame is embedded within a layer of the material. Material 54 is typically configured to impede blood flow therethrough, as described in further detail hereinbelow. For some applications, the frame of the stent graft material is a braided stent. For some applications, the braided stent provides flexibility to the device that facilitates insertion of the device via curved portions of the vasculature. For some applications, using a braided stent allows the device to be radially constrained to a narrower diameter than would be possible using a non-braided stent.

For some applications, material 54 is impermeable and prevents blood from flowing back toward the aortic valve during systole (and/or during diastole), outside of the conduit. Alternatively, material 54 is not impermeable, but has a permeability that is sufficiently low as to substantially prevent any blood from flowing through the longitudinal portion of the aorta, via any flow path other than through the conduit defined by the inner surface of the device, in the manner described hereinabove. For some applications, the material has permeability per unit length of less than 0.25 micrometers (i.e., between 0 and 0.25 micrometers), where the permeability per unit length is defined based upon the following equation, which is based upon Darcy's Law: $k/\Delta x = V\mu/\Delta p$, where k is permeability, $\Delta x$ is length (in meters), V is average velocity (in meters per second), $\mu$ is fluid viscosity (measured in Pascal-seconds), and $\Delta P$ is the pressure differential measured in Pascals).

For some applications, material 54 is structured such that there are open spaces between portions of the material. For example, the material may be arranged in a lattice structure, a braided structure, a crisscross structure, a woven structure, a cellular structure, a stitched structure, or a similar structure. Typically, even for such applications, more than 20 percent of the area of each of the surfaces is filled with material, and less than 80 percent of the area of each of the surfaces is open space between the material. Further typically, more than 50 percent, e.g., more than 80 percent, of the area of each of the surfaces is filled with material. For some applications, there are no open spaces within the surfaces (i.e., the entirety of each of the surfaces is filled with material).

For some applications, inner surface 24 that defines conduit 26 is rough. The rough surface of the conduit is configured to act as a turbulator on the boundary layer between the blood and the surface of the conduit, such as to increase adhesion, excite the boundary layer, and delay flow separation.

For some applications, by virtue of having both upstream and downstream outer surfaces, pressure-loss-reduction device 20 is configured to trap any blood that is disposed within a region 36 (FIG. 1A) between the conduit and the inner wall of the aorta within the longitudinal portion of the aorta in which the device is placed. In this manner, the device is configured to prevent any thrombi that develop within region 36 from exiting the region and entering the subject's bloodstream.

For some applications, the device is configured to promote coagulation of blood that is disposed within region 36 between the conduit and the inner wall of the aorta within the longitudinal portion of the aorta in which the device is placed, by substantially reducing blood flow through this region relative to blood flow through this region in the absence of the device. Typically, the material that defines the upstream outer surface, the downstream outer surface and/or the inner surface is configured to prevent any thrombi that develop within the region from exiting the region and entering the subject's bloodstream. For some applications, by promoting the coagulation of blood within the region, the device causes blood entering the region to become coagulated, such that the region becomes filled with coagulated blood within a given time period of the device being placed within the aorta (e.g., within one week, one month, or three months of the device being placed within the aorta), such that the coagulated blood impedes (e.g., blocks) the flow of blood through the region.

For some application, the blood that becomes coagulated within the region is blood that became trapped within the region immediately upon deployment of the device. Alternatively or additionally, blood enters the region subsequent to the device having been deployed, and the blood that subsequently enters the region becomes coagulated. It is noted that, even for such applications, the upstream and downstream surfaces are configured such that, even when the device is first deployed and before coagulated blood has formed inside the region, flow via flow paths other than through the conduit defined by the inner surface of the device is less than 20 percent (e.g., less than 10 percent, or less than 5 percent) of total blood flow through the longitudinal portion of the subject's aorta. For some applications, techniques are applied in order to coagulate blood that is trapped within region 36. For example, coil compaction techniques may be applied in order to cause the blood to coagulate.

Typically, when device 20 is deployed inside the subject's ascending aorta, blood is supplied to the subject's coronary arteries 38 via backflow of blood through conduit 26 during diastole, and/or via blood flowing directly from the aortic valve to the coronary arteries without passing into conduit 26 (not shown). For some applications, a portion of the blood supply to the coronary arteries is provided by antegrade blood flow from the aortic valve to the coronary arteries (e.g., during systole). Typically, most of the blood supply to the coronary arteries is via the backflow of blood through conduit 26 during diastole.

As described hereinabove above, at least a portion of conduit 26 diverges in a direction from upstream end 30 of the conduit to downstream end 34 of the conduit. Due to the divergence of the portion of the conduit, the cross-sectional area of the downstream end of the diverging portion of the conduit is greater than the cross-sectional area of the upstream end of the conduit. Typically, the conduit is divergent over more than 50 percent, e.g., more than 75 percent, or more than 90 percent, of the total length of the conduit, (i.e., the diverging portion comprises more than 50 percent, e.g., more than 75 percent, or more than 90 percent, of the total length of the conduit). Further typically, the conduit is divergent over more than 50 percent, e.g., more than 75 percent, or more than 90 percent, of the total length of the device, (i.e., the diverging portion comprises more than 50 percent, e.g., more than 75 percent, or more than 90 percent, of the total length of the device). For some applications, the divergence of the conduit is at a constant angle along the length of the diverging portion of the conduit, for example, such that the diverging portion of the conduit defines a frustoconical shape. For some applications, the angle of the divergence of the conduit along the diverging portion of the conduit changes along the length of the diverging portion of the conduit. For example, the angle of the divergence may increase from the upstream end of the portion to the downstream end of the portion, such that inner surface 24 has a convex cross-section along the diverging portion of the conduit. For some applications, the diverging portion of the conduit defines a Stratford ramp shape. Typically, the upstream and downstream ends of the diverging portion of the conduit define circular cross-sections. Alternatively, the upstream and downstream ends of the diverging portion of the conduit define elliptical cross-sections, polygonal cross-sections, or differently shaped cross-sections.

For some applications, at each of the upstream and downstream ends of the aortic pressure-loss-reduction device, frame 52 of the device defines a folded portion 56U and 56D at the transition between the intermediate portion 23 of the device (which has inner surface 24 that defines conduit 26) and, respectively, the upstream anchor 33 and the downstream anchor 31. For example, as shown, the frame of the device may form folded portions 56UF and 56DF that have sinusoidal (i.e., S-shaped) cross-sectional shapes.

Typically, due to folded portion 56U, along the longitudinal direction of the device, there is partial overlap between upstream anchor 33, and conduit 26. For some applications (not shown), upstream folded portion 56U is such that the upstream end of conduit 26 extends proximally beyond the upstream end of upstream anchor 33. Typically, the upstream end of upstream anchor 33 is placed within the aorta downstream of the aortic sinuses. For some applications, the upstream end of the conduit extends proximally beyond the upstream end of upstream anchor, such that the upstream end of the conduit is closer to the aortic valve than the upstream end of the upstream anchor. For some applications (not shown), the upstream anchor extends distally such that it overlaps with most of (e.g., all of) conduit 26. Typically, due to folded portion 56D, along the longitudinal direction of the device, there is partial overlap between downstream anchor 31, and conduit 26. For some applications (not shown), downstream folded portion 56D is such that the downstream end of conduit 26 extends distally beyond the downstream end of downstream anchor 31. For some applications (not shown), downstream anchor 31 extends proximally such that it overlaps with most of (e.g., all of) conduit 26.

For some applications, the folded portions enhance sealing between the anchors of the device and the aorta (relative to if the device did not include folding portions, ceteris paribus), by enhancing the radial force that the anchors of the device exert upon the inner wall of the aorta. For example, the folded portions may enhance the radial force since, at the folded portions there are effectively two or more layers applying a radial force to the inner wall of the aorta, and/or due to the shape of the fold itself adding to the outward radial force that is exerted upon the inner wall of the aorta. Moreover, at the folded portions there is typically a portion of frame 52 that extends in the radial direction, or at least extends at an angle that includes a strong radial component. Typically, this portion of the frame enhances the radial force that the anchors of the device exert upon the inner wall of the aorta, in a similar manner to how a spoke of a wheel enhances the radial strength of the wheel.

For some applications, due to the both the upstream and downstream ends of device 20 including folded portions, intermediate portion 23 of the device, which defines conduit 26, is (a) on the one hand, longitudinally fixed with respect to the aorta by the upstream and downstream portion exerting radial forces against the inner wall of the aorta (the radial forces being reinforced by the folded portions), but (b) on the other hand, able to adjust the angle that the longitudinal axis of the intermediate portion makes with the longitudinal axis of the upstream and downstream portions, by the folded portions acting as hinges about which the intermediate portion can flex. In this manner, the intermediate portion of the device is able to adjust its angular position with respect to the aorta, and/or be disposed at an angle with respect to the local longitudinal axis of the aorta at the longitudinal locations at which the upstream and/or downstream portions are fixed to the aorta.

For some applications, by virtue of the intermediate portion being separated from the upstream and downstream portions, the length of the intermediate portion typically does not change even if the distance between the upstream and downstream portion changes (e.g., due to movement of the wall of the aorta). For some applications, frame 52 is configured such that in the event that the diameter of the upstream anchor changes, the diameter of conduit 26 does not change by the same amount, as described in further detail hereinbelow with reference to FIGS. 3A-B.

Typically, upstream folded portion 56U of frame 52 with material 54 coupled thereto acts as upstream outer surface 28, as described hereinabove, and is configured to impede antegrade and/or retrograde blood flow around the outside of the upstream end of the conduit. Further typically, downstream folded portion 56D of frame 52 with material 54 coupled thereto acts as downstream outer surface 32, as described hereinabove, and is configured to impede antegrade and/or retrograde blood flow around the outside of the downstream end of the conduit. It is noted that folded portion 56D is typically configured such that at any given radial location along the folded portion, there is only one layer of the stent graft material (a layer of stent graft material typically including a frame and covering material, as described hereinabove) impeding blood flow around the outside of the downstream end of the conduit. Similarly, folded portion 56U is typically configured such that at any given radial location along the folded portion, there is only one layer of the stent graft material impeding blood flow around the outside of the upstream end of the conduit.

Figure 2A:
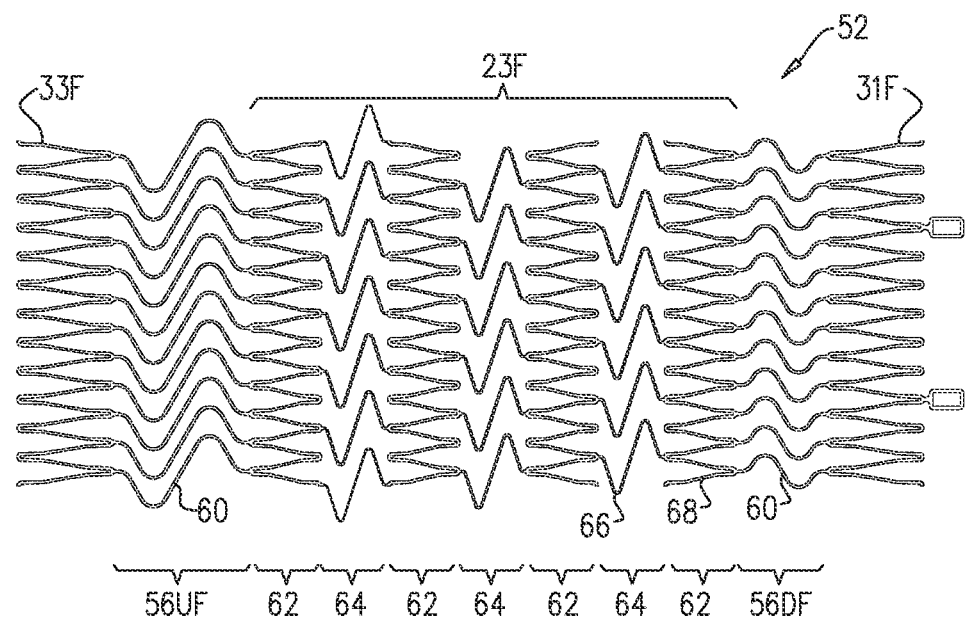
FIGS. 2A, 2B, and 2C are schematic illustrations of frames of a pressure-loss-reduction device configured to assume a curved configuration upon being deployed within a subject's ascending aorta, in accordance with some applications of the present invention.
Figure 2B:
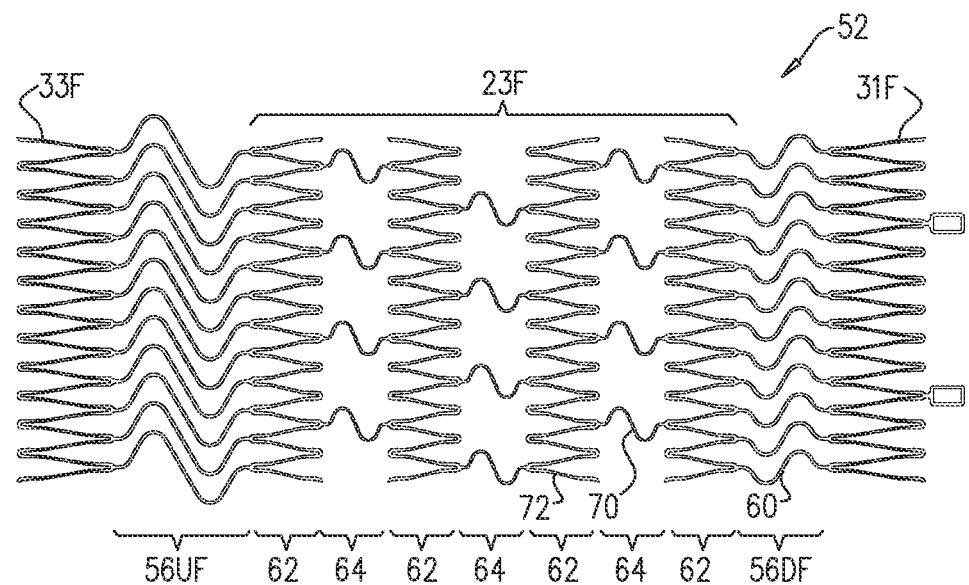
Figure 2C:
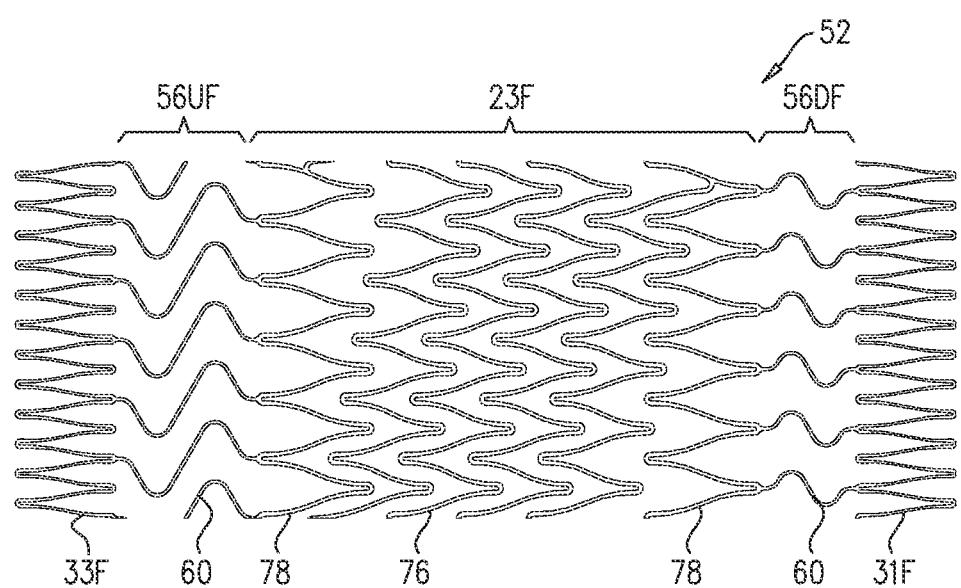

Reference is now made to FIGS. 2A, 2B, and 2C, which are schematic illustrations of frames 52 of pressure-loss-reduction device 20, in accordance with some applications of the present invention. Each of FIGS. 2A-2C shows a flattened profile of the device frame, in accordance with some applications of the present invention. As described hereinabove, for some applications, device 20 is formed from a single continuous portion of graft material. The graft material is typically formed from a combination of frame 52, which is typically a metal or alloy frame (e.g., a stent made of stainless steel or nitinol or cobalt chromium), and covering material 54, e.g., a fabric and/or a polymer (such as expanded polytetrafluoroethylene (ePTFE), or woven, knitted and/or braided polyester), which is typically coupled to the inside of the frame via stitching, spray coating, encapsulation, electrospinning, dip molding and/or a different technique. In accordance with some applications, a layer of the material is coupled to the inside of at least a portion of the frame, the outside of at least a portion of the frame, and/or at least a portion of the frame is embedded within a layer of the material. The profiles shown in FIGS. 2A-C depicts (for illustrative purposes) how the frame of the device would appear if, prior to shape setting the frame, a longitudinal incision was to be made along the length of the frame at a given circumferential location of the frame, and the frame were to then be laid out flat upon a surface.

As shown in each of FIGS. 2A-C, the frame typically comprises an upstream anchor frame portion 33F (corresponding to upstream anchor 33), a downstream anchor frame portion 31F (corresponding to downstream anchor 31), and intermediate frame portion 23F (corresponding to the intermediate portion of the device, inner surface 24 of which defines conduit 26). Typically, at frame portion 56UF and 56DF corresponding to folded portions 56U and 56D (i.e., between upstream anchor frame portion 33F and intermediate frame portion 23F, and between downstream anchor frame portion 31F and intermediate frame portion 23F), the frame defines sinusoidal struts 60. Typically, the folded portions are formed by shape setting the sinusoidal struts into the desired folded shape. For some applications, the sinusoidal struts facilitate shape setting the frame of device 20 to include folded portion 56U and 56D, such that the radius of curvature of the curve made by the folded portion is smaller than if the folded portion were to be formed solely by shape setting a straight strut, as described in further detail hereinbelow with reference to FIG. 14A. For some applications, the folded portion can thereby be longer, such as to enhance sealing with respect to the aorta that is provided by the folded portion, as described hereinabove. For some applications, allowing upstream folded portion 56U to be longer facilitates placement of the upstream end of the conduit closer to the orifice of the aortic valve, by allowing greater overlap between the conduit and the upstream anchor.

As indicated in FIGS. 2A-C, typically sinusoidal struts 60 at frame portion 56UF corresponding to the upstream folded portion 56U are longer than those at frame portion 56DF corresponding to downstream folded portion 56D. For example, the ratio of the lengths of the sinusoidal struts corresponding to the upstream folded portion 56U to lengths of the sinusoidal struts corresponding to downstream folded portion 56D may be more than 5:4, or more than 3:2, or more than 2:1. Referring again to FIG. 1B, the difference between the diameter of the conduit at the upstream end and the diameter of the upstream anchor, is greater than the difference between the diameter of the conduit at the upstream end and the diameter of the upstream anchor. Therefore, the struts corresponding to the upstream folded portion are longer than those corresponding to the downstream portion. Furthermore, as described hereinabove, it is typically desirable for the upstream end of the conduit to overlap with the upstream anchor, such that the upstream end of the conduit is placed as close as possible to the orifice of the aortic valve. For some applications, the sinusoidal struts corresponding to the upstream folded portion are configured to have a length that is such as to facilitate the requisite degree of overlap between the conduit and the upstream anchor.

A portion 23F of the frame that corresponds to intermediate portion 23 of pressure-reduction-loss device 20 (i.e., the portion of the device that defines conduit 26) is typically configured to provide the characteristics described hereinabove. Namely, that (a) least a portion of the conduit diverges in a direction from an upstream end of the conduit to a downstream end of the conduit, such that the cross-sectional area of the conduit at the downstream end is greater than the cross-sectional area of the conduit at the upstream end, and (b) at least upon being placed inside the subject's ascending aorta, the conduit is curved (i.e., the conduit defines a curved longitudinal axis), such as to conform at least partially to the curvature of the ascending aorta. In the examples of frame 52 as shown in FIGS. 2A, 2B, and 2C, portion 23F of the frame corresponding to intermediate portion 23 is configured to provide these functionalities, but the examples shown in each of the figures differ from each other. In particular, portion 23F of the frame in the examples shown in FIGS. 2A-2C is configured to be flexible, such that upon being placed within the ascending aorta, the intermediate portion of device 20 curves to conform with the shape of the ascending aorta.

With reference to FIGS. 2A and 2B, for some applications, device 20 is configured to curve, such as to conform with curvature of the ascending aorta, at least partially by virtue of portion 23F of frame 52 (i.e., the portion of the frame that corresponds to intermediate portion 23 of pressure-loss-reduction device 20) being cut such that the portion defines alternating rows of struts. A density of the struts (i.e., the number of struts per unit circumference of the frame) in a first set 62 of the alternating rows of struts is greater than the density of the struts in the second set 64 of the alternating rows of struts, with the first set and second set of struts alternating with each other along the length of the portion of frame 52 corresponding to intermediate portion 23. For example, as shown in FIG. 2A, in the second set of the alternating rows of struts, there may be one strut 66 corresponding to every 4 struts 68 of the first set of the alternating rows of struts. Or, as shown in FIG. 2B, in the second set of the alternating rows of struts, there may be one strut 70 corresponding to every 6 struts 72 of the first set of the alternating rows of struts. For some applications, the struts of the second set of the alternating rows of struts are shaped differently from the struts of the first set of alternating rows of struts. For example, as shown, the struts of the second set of the alternating rows of struts may be sinusoidal, whereas the struts of the first set of alternating rows of struts may be straight. Typically, the lower strut density of the struts within the second set of alternating rows of struts, and/or the shapes of the struts within the second set of alternating rows of struts facilitates curving of intermediate portion 23F of frame 52, such as to conform with curvature of the ascending aorta, by providing flexibility to the portion of the frame. Alternatively or additionally, other techniques are used to provide the second set of the alternating rows of struts with greater flexibility than the first set of the alternating rows of struts. For example, the widths of the struts in the second set of the alternating rows of struts may be less than that of the first set of the alternating rows of struts.

For some applications (not shown), device 20 is configured in a generally similar manner to that described with reference to FIGS. 2A-B, except that at locations corresponding to the second set of the alternating rows of struts, there are no struts, and the stent graft at those locations comprises only the covering material layer (e.g., the fabric layer), without any frame. In general, for some applications, the covering material of the stent graft is configured to cause the frame to curve in a manner that conforms with the curvature of the aorta. For example, the covering material may be shaped in a curved shape, and/or may be coupled to the frame in a manner that causes the frame to curve in a manner that conforms with the curvature of the aorta.

With reference to FIG. 2C, for some applications, device 20 is configured to curve, such as to conform with curvature of the ascending aorta, at least partially by virtue of portion 23F of frame 52 (i.e., the portion of the frame that corresponds to intermediate portion 23 of pressure-loss-reduction device 20) including a spiraling set of struts 76. For example, as shown, portion 23F may define a zigzag strut configuration that spirals around the portion of the frame that corresponds to intermediate portion 23 of the device. For some applications, at either end of portion 23F of the frame (i.e., at the locations that are adjacent to sinusoidal struts corresponding to folded portions 56U and 56D), the frame includes complete rows 78 of struts. For such applications, the spiraling set of struts extends from the upstream complete row of struts to the downstream complete row of struts. The complete rows of struts at either end of the intermediate portion typically provide the ends of the portion with radial strength, such that the ends of the portion do not become radially compressed, while the spiraling set of struts provides the intermediate portion with flexibility. Typically, along the spiraling set of struts, each row of struts in the spiral is not connected to adjacent rows of the spiral, such that each row of struts is able to flex with respect to the adjacent row.

For some applications (not shown), frame 52 is cut such that the frame is non-axisymmetric about its longitudinal axis. For example, the frame may be cut such that a side of the frame that is configured to be placed on the inside of the curve of the aorta is shorter than the side of the frame that is configured to be placed on the outside of the curve. For some such applications, the frame is constructed from struts that are arranged in closed cells and/or struts that are shaped as described with any one of FIG. 2A-2C, or 3A-3B, such as sinusoidal struts, spiral struts, and/or zigzagging struts. By cutting the frame such that the frame is non-axisymmetric about its longitudinal axis and then applying shape-setting techniques to the frame, the frame is typically configured such that, in the non-constrained configuration of the device, intermediate portion 23 of the device (which has inner surface 24 that defines conduit 26) is configured to be curved (e.g., as shown in FIG. 12B). For some applications, by cutting the frame such that the frame is non-axisymmetric about its longitudinal axis and then applying shape setting techniques to the frame, the frame is configured such that, in the non-constrained configuration of the device, intermediate portion 23 of the device (which has inner surface 24 that defines conduit 26) is configured to be disposed at an angle with respect to upstream anchor 33 (i.e., such that the longitudinal axis of the conduit forms an angle with respect to the longitudinal axis of the upstream anchor), but the conduit is not curved (e.g., as shown in FIG. 12C). For some applications, device 20 as shown in FIG. 12C is configured such that the conduit becomes curved upon being placed in the ascending aorta, such as to conform to the curvature of the ascending aorta.

Figure 3A:
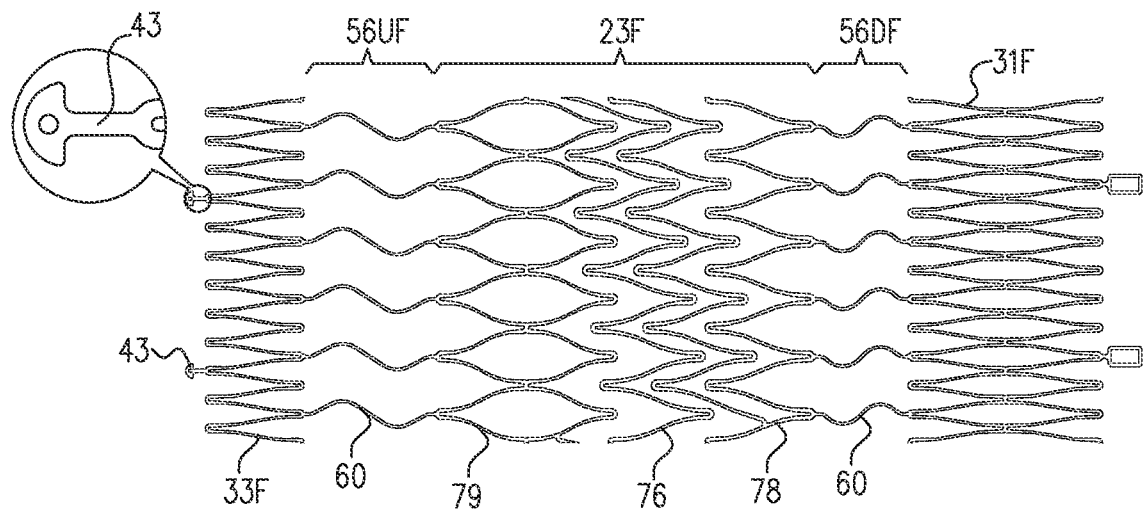
FIGS. 3A and 3B are schematic illustrations of frames of a pressure-loss-reduction device configured such that, in the event that the diameter of an upstream anchor of the device changes, the diameter of the upstream end of a conduit of the device does not change by the same amount, in accordance with some applications of the present invention.
Figure 3B:
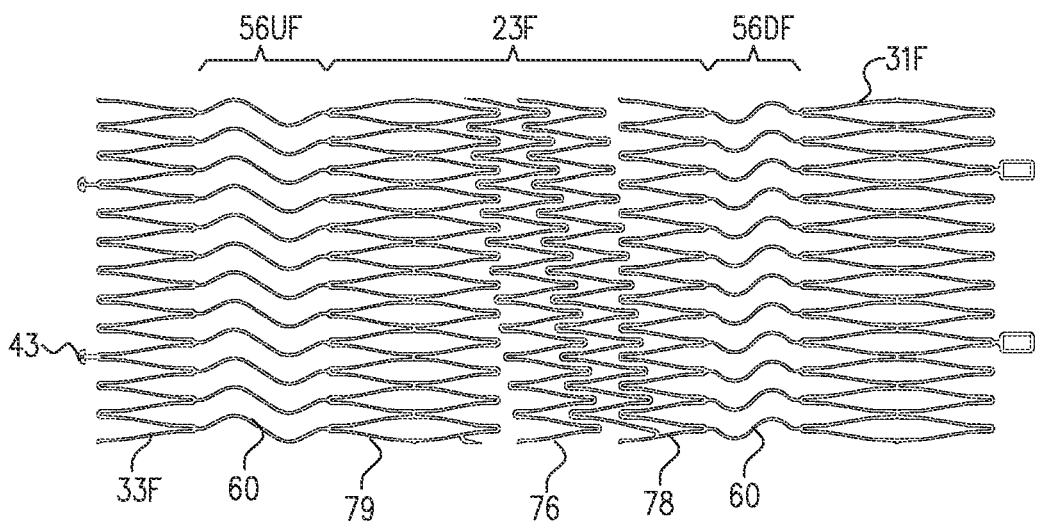

Reference is now made to FIGS. 3A and 3B, which are schematic illustrations of frames 52 of a pressure-loss-reduction device 20 configured such that in the event that the diameter of upstream anchor 33 of the device changes, the diameter of the upstream end 30 of conduit 26 of the device does not change by the same amount, in accordance with some applications of the present invention. The frame as shown in FIGS. 3A and 3B is generally similar to that shown in FIG. 2C, except for the differences described hereinbelow. Typically, device 20 is configured to curve, such as to conform with curvature of the ascending aorta, at least partially by virtue of portion 23F of frame 52 (i.e., the portion of the frame that corresponds to intermediate portion 23 of pressure-loss-reduction device 20) including a spiraling set of struts 76. For example, as shown, portion 23F may define a zigzag strut configuration that spirals around the portion of the frame that corresponds to intermediate portion 23 of the device. For some applications, at the downstream end of portion 23F of the frame (i.e., at the location that is adjacent to sinusoidal struts corresponding to folded portion 56D), the frame includes a complete row 78 of struts, as described hereinabove, with reference to FIG. 2C. For some applications, at the upstream end of portion 23F of the frame (i.e., at the location that is adjacent to sinusoidal struts corresponding to folded portion 56U), the frame includes a complete row 79 of closed cells.

It is typically desirable that the diameter of upstream end 30 of conduit 26 does not change substantially, since the diameter of the upstream end of the conduit is typically sized to correspond to the orifice of the subject's aortic valve. However, the upstream anchor typically undergoes variations in its diameter, for example, due to variations in pressure that is exerted upon the upstream anchor over the course of the subject's cardiac cycle. Therefore, for some applications, at the upstream end of portion 23F of the frame, the frame is reinforced relative to at least some of the rest of portion 23F (e.g. relative to a longitudinally-central portion of the intermediate portion). For example, as shown in FIGS. 3A and 3B, the frame may include a complete row 79 of closed cells at the upstream end of portion 23F of the frame. In this manner, the diameter of the upstream end of the conduit is stabilized and less susceptible to changes.

Experiments were conducted by the inventors of the present application, in which they measured the ratio between the change of diameter that the upstream end of the device underwent in response to changes in the diameter of the upstream anchor. It was found that when using a device as shown in FIGS. 3A-B in which the upstream anchor had an initial diameter of 30 mm and the upstream end of the conduit has an initial diameter of 14.5 mm, then in response to the diameter of the upstream anchor being reduced by 5 mm (to 25 mm), the diameter of the upstream end of the conduit decreased by less than 2 mm, and in some cases as little as 1.5 mm Thus, in accordance with some applications of the present invention, the upstream end of intermediate portion 23F of the frame is reinforced, such that, a ratio of the decrease in the absolute diameter of the upstream end of conduit 26 to the decrease in the absolute diameter of the upstream anchor is less than 1:2, e.g., less than 1:3, less than 1:4, or less than 1:5.

For some applications, alternative or additional techniques to those shown in FIGS. 3A and 3B are used to reinforce the upstream end of intermediate portion 23F of the frame, relative to at least some of the rest of portion 23F (e.g. relative to a longitudinally-central portion of the intermediate portion). For example, struts that are shorter and/or wider than those used in the rest of intermediate portion 23F may be used at the upstream end of intermediate portion 23F. Alternatively or additionally, a greater number of cells and/or struts may be used in the upstream-most row (or the first number of upstream-most rows) of intermediate portion 23F, than are used in other rows of intermediate portion 23F.

For some applications, the flexibility of the sinusoidal struts 60 in portion 56UF of the frame is configured such that the decrease in the absolute diameter of the upstream end of conduit 26 in response to a decrease in the absolute diameter of the upstream anchor is less than the decrease in the absolute diameter of the upstream anchor. That is to say that the sinusoidal struts are made to be flexible such that they absorb at least some of the change in the diameter of the upstream anchor, without conveying the entire change in the diameter to the upstream end of the conduit. It is noted that, typically, by increasing the flexibility of the sinusoidal struts, the radial force that the anchor exerts on the inner wall of the aorta is decreased. As such, by using the flexibility of the sinusoidal struts to stabilize the diameter of the upstream end of the conduit, there is a tradeoff between the stabilization of the diameter of the upstream end of the conduit, and the radial force that the anchor is able to exert on the inner wall of the aorta. By contrast, reinforcing the upstream end of portion 23F of the frame as described hereinabove typically results in the diameter of the upstream end of the conduit being stabilized as well as the radial force that the anchor exerts on the inner wall of the aorta being increased. Therefore, for some applications, the diameter of the upstream end of the conduit is stabilized by reinforcing the upstream end of portion 23F of the frame, as described hereinabove.

For some applications, device 20 includes one or more projections 43 that project from an upstream end of portion 33F of frame 52 (which corresponds to upstream anchor 33), as shown in FIG. 3A-3B. The projections are described in further detail hereinbelow with reference to FIGS. 4A-5D.

Figure 4A:
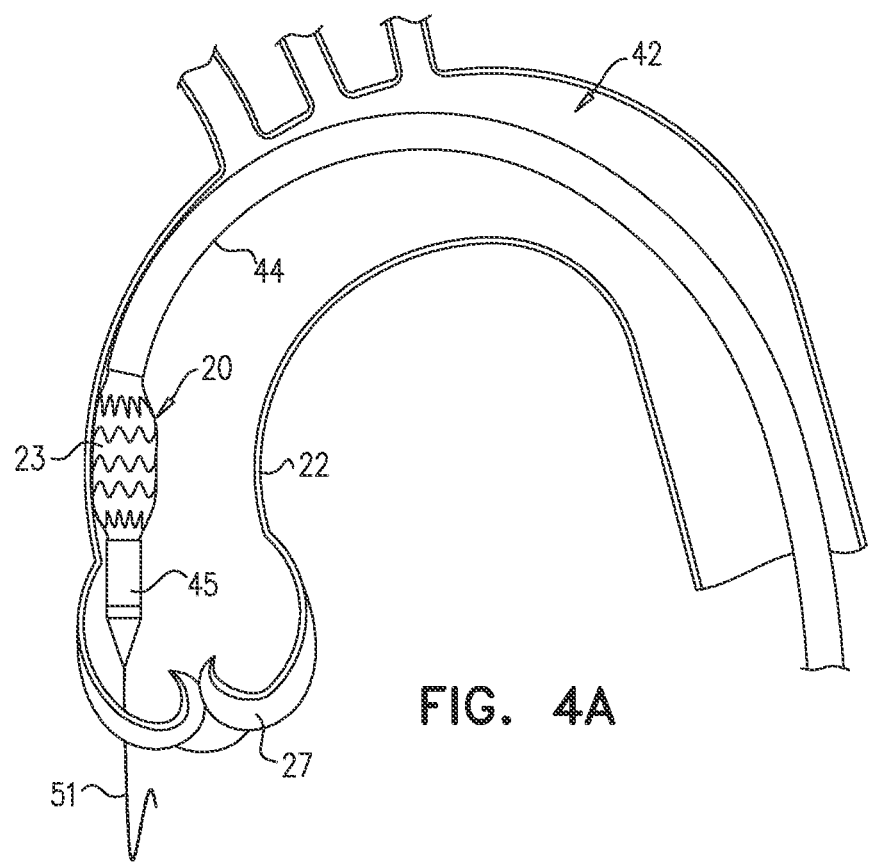
FIGS. 4A, 4B, 4C, and 4D are schematic illustrations of respective steps of a method for implanting a pressure-loss-reduction device in a subject's ascending aorta, in accordance with some applications of the present invention.
Figure 4B:
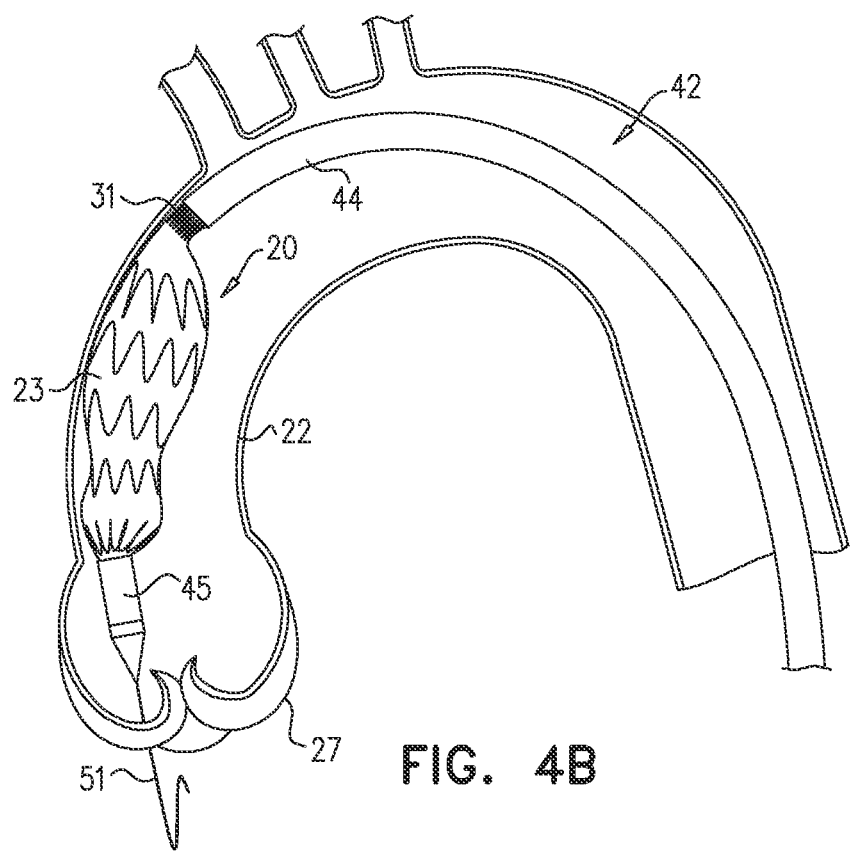
Figure 4C:
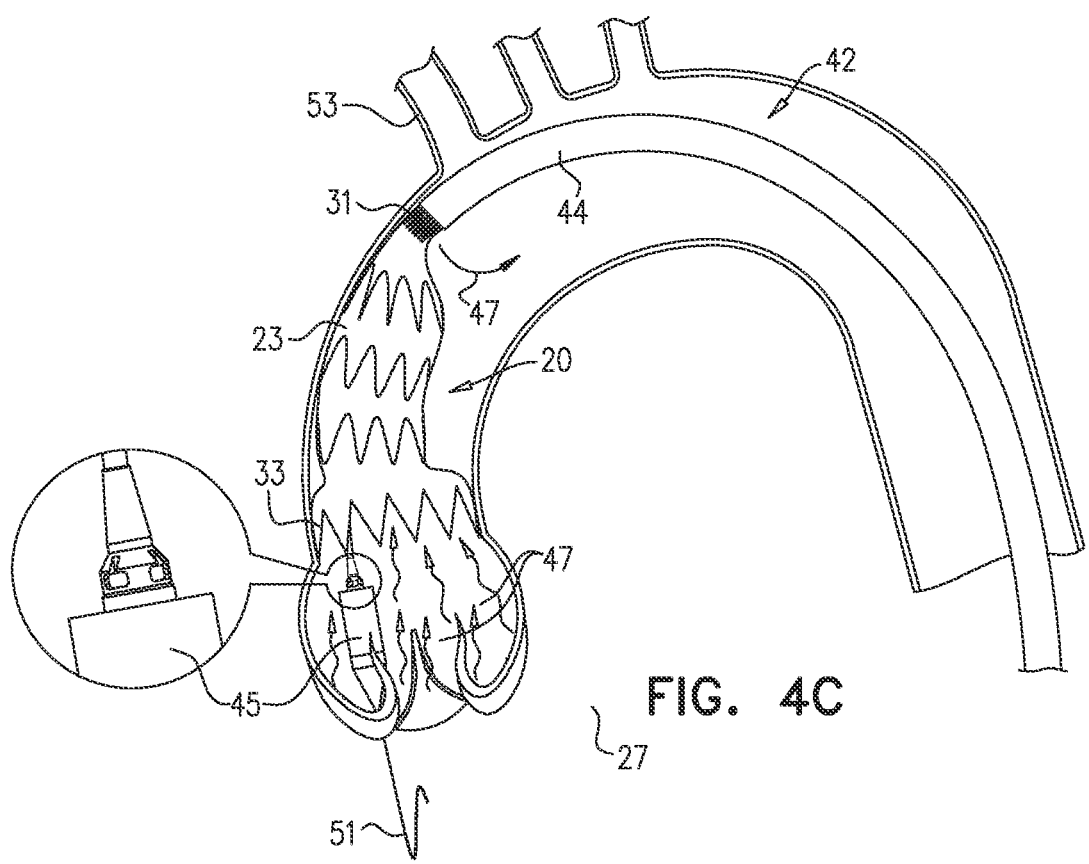
Figure 4D:
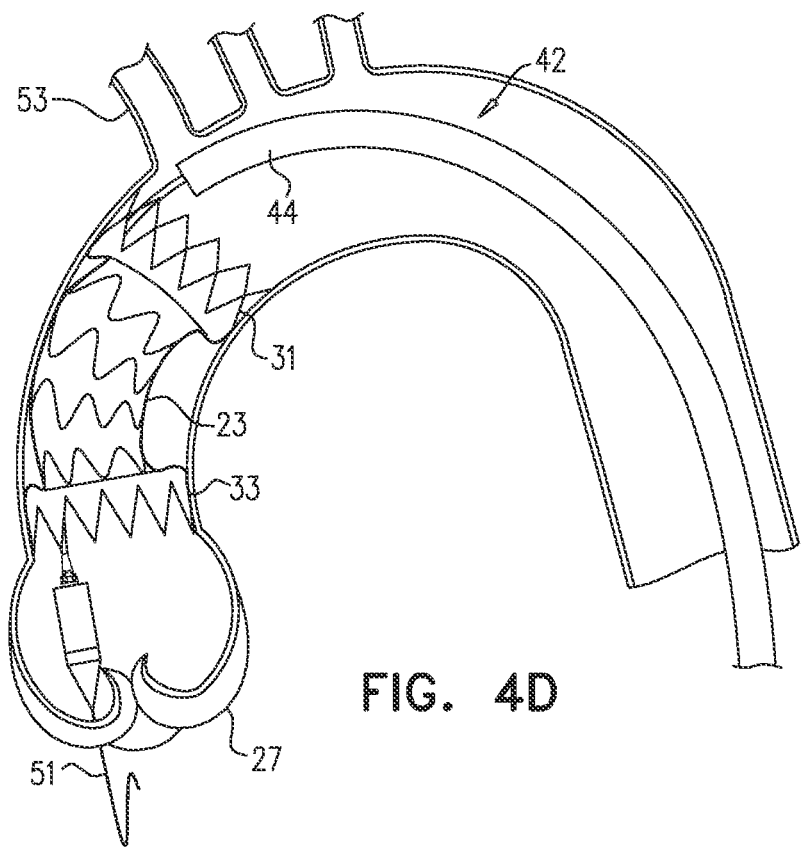
Figure 5A:
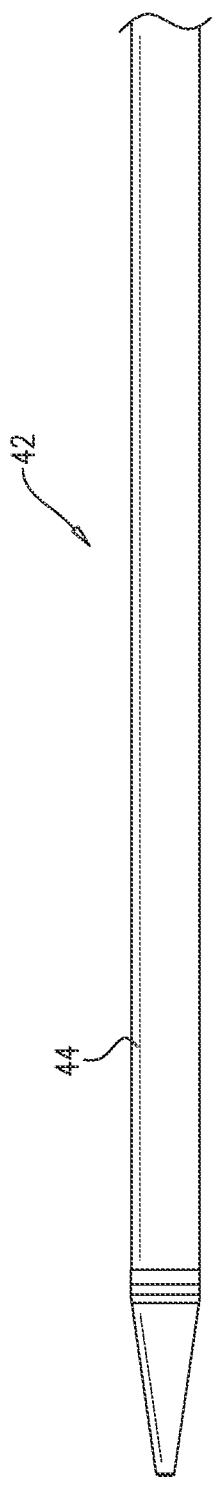
FIGS. 5A, 5B, 5C, and 5D are schematic illustrations of a delivery device that is configured to deploy a pressure-loss-reduction device in a subject's ascending aorta, in accordance with some applications of the present invention.
Figure 5B:
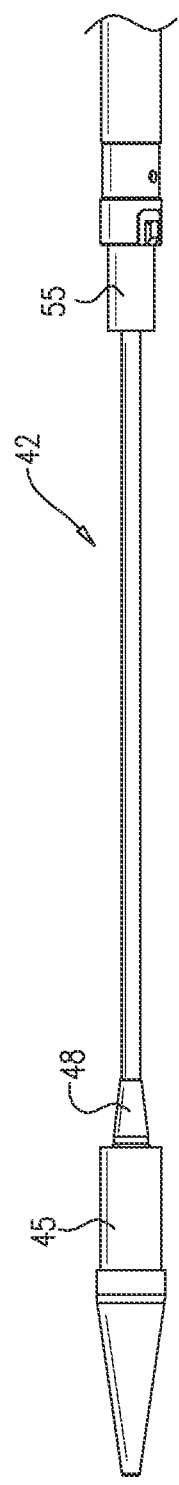
Figure 5C:
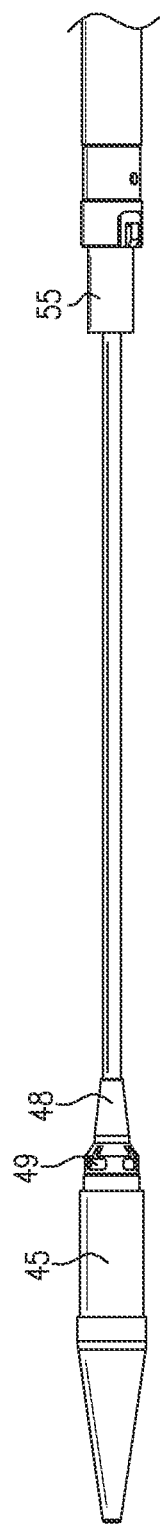
Figure 5D:
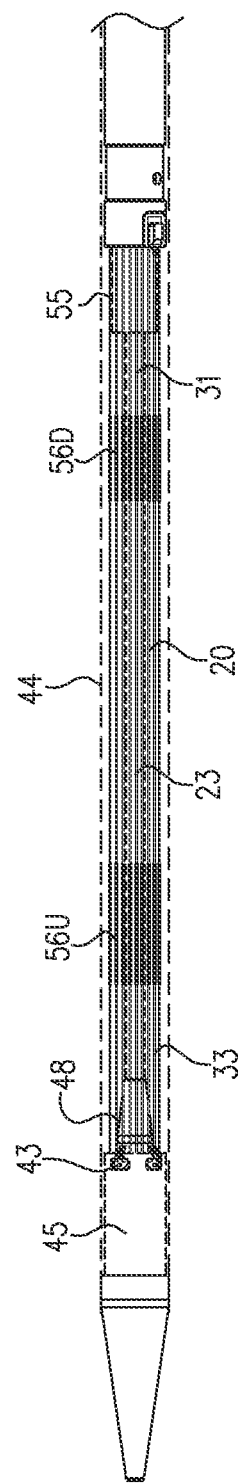

Reference is now made to FIGS. 4A, 4B, 4C, and 4D, which are schematic illustrations of respective steps of a method for implanting pressure-loss-reduction device 20 in a subject's ascending aorta 22, in accordance with some applications of the present invention. Typically, the device is introduced while the device is disposed in a radially-constrained configuration inside a delivery device, such as a catheter 42. Reference is also made to FIGS. 5A, 5B, 5C, and 5D, which are schematic illustrations of catheter 42, in accordance with some applications of the present invention. FIG. 5A shows how the catheter appears when device 20 is disposed inside the catheter. FIG. 5B shows the how the catheter appears in the absence of a covering sheath 44 of the catheter, and in the absence of device 20, for illustrative purposes. FIG. 5C shows the how the catheter appears in the absence of a proximal covering sheath 44 of the catheter, in the absence of device 20, and with a distal covering sheath 45 of the catheter advanced distally with respect to a mount 48 of the catheter, such as to expose recesses 49 defined by the mount, for illustrative purposes. FIG. 5D shows device 20 disposed inside catheter 42, the device being constrained into a radially-constrained configuration by proximal covering sheath 44 and by distal covering sheath 45 of the catheter. In the view shown in FIG. 5D, proximal covering sheath 44 and distal covering sheath 45 of the catheter are transparent, for illustrative purposes.

In the radially-constrained configuration of the device, the device frame is typically generally cylindrical, with folded portions 56U and 56D being unfolded, as shown in FIG. 5D. Typically, the catheter is guided over a guidewire 51, until the distal tip of the catheter is disposed at the subject's aortic valve 27. Typically, device 20 is self-expandable and is configured to radially expand upon being released from the delivery device. (It is noted that, for some applications, the device does not expand such as to fully assume its non-constrained configuration, since upon being released inside the ascending aorta, the device is at least partially constrained by the aorta.)

Typically, the catheter is inserted into the ascending aorta via the aortic arch, with the upstream anchor (which is the portion of the device that typically placed closest to the subject's aortic valve) being disposed at the distal end of the catheter. The inventors of the present application found that if upstream anchor 33 of device 20 is allowed to radially self-expand, and then, subsequently, intermediate portion 23 is allowed to radially expand, the radial expansion of the intermediate portion against the inner wall of the ascending aorta (which is typically curved) sometimes results in the upstream anchor becoming displaced. Typically, it is desirable for device 20 to be deployed within the aorta such that a plane defined by the upstream end of conduit 26 is parallel with a plane defined by the subject's aortic valve orifice (and/or such that the plane defined by the upstream end of conduit 26 is parallel with a plane defined by the subject's sinotubular junction). In some cases, even though the upstream anchor was initially positioned such that the upstream end of conduit 26 was parallel with the subject's aortic valve orifice, the upstream anchor became displaced from that position, such that the upstream end of the conduit was disposed at an angle with respect to the aortic valve orifice. Therefore, for some applications, intermediate portion 23 of device 20 is at least partially released from its radially-constrained configuration, prior to upstream anchor 33 being released from its radially-constrained configuration.

For some applications, device 20 includes projections 43 from the upstream end of the upstream anchor (shown in FIGS. 3A and 3B for example). For example, the projections may be T-shaped projections, as shown. The intermediate portion of device 20 is at least partially released from its radially-constrained configuration by proximal covering sheath 44 of the catheter being retracted with respect to the intermediate portion. While the intermediate portion is released from its radially-constrained configuration, the upstream anchor is configured to be maintained in its radially-constrained configuration, e.g., by the T-shaped projections being held within distal covering sheath 45 of catheter 42. The transition from FIG. 4A to FIG. 4B illustrates the partial release of the intermediate portion from its radially-constrained configuration, while the upstream anchor is held in a radially-constrained configuration.

For some applications, at the downstream end of downstream anchor 31, cells of frame 52 do not have material 54 coupled to them, but rather are open cells (as shown in FIG. 1B, for example). Typically, prior to the upstream anchor being released from its radially-constrained configuration, proximal covering sheath 44 of the catheter is retracted, such that at least a portion of the open cells at the downstream end of the downstream anchor are uncovered. Subsequently, the upstream anchor is released from its radially-constrained configuration (e.g., by distal covering sheath 45 of the catheter being advanced distally, such as to release projections 43), as shown in the transition from FIG. 4B to FIG. 4C (and as shown, in the absence of device 20, in the transition from FIG. 5B to FIG. 5C). At this stage, even though the downstream end of the device has not been fully released from the catheter, there is at least some blood flow through the device, the blood being able to exit the downstream end of the device via the open cells at the downstream end of the downstream anchor. This is illustrated by blood flow arrows 47 in FIG. 4C. For some applications, at this stage, device 20 is still repositionable, for example, in the event that the device has been deployed at the wrong position. Alternatively or additionally, at this stage, device 20 is still retrievable into catheter 42, for example, in the event that the device has been deployed at the wrong position. Subsequently, proximal covering sheath 44 of the catheter is further retracted, such as to release downstream anchor 31. At this stage, device 20 is fully deployed and anchored within the subject's aorta, as shown in FIG. 4D. Subsequently, catheter 42 is withdrawn from the subject aorta.

For some applications, device 20 is held within catheter 42 between proximal covering sheath 44 and central mount 48, and between distal covering sheath 45 and the central mount. Typically, mount 48 defines recesses 49 that match the shapes of projections 43 from the upstream end of upstream anchor 33. The projections are held within the recesses by distal covering sheath 45. Typically, subsequent to device 20 being deployed and anchored within the aorta, distal covering sheath 45 and a distal portion of mount 48 are retracted from the subject's ascending aorta via conduit 26 of device 20. For some applications, the distal portion of mount 48 has a conical shape in order to facilitate retraction of the distal portion of the mount 48 and distal covering sheath 45 of the catheter via the conduit. For some applications, the angle of convergence of the mount varies along the length of the mount in order to accommodate portions of device 20 having varying thicknesses (in the radially-constrained configuration of device 20) between the mount and proximal and distal covering sheaths 44 and 45 of the catheter.

Referring again to FIGS. 5B-D, as described hereinabove, for some applications, at the downstream end of downstream anchor 31, cells of frame 52 do not have material 54 coupled to them, but rather are open cells (as shown in FIG. 1B, for example). Typically, since the cells at the downstream end of downstream anchor 31 do not have material coupled to them, a tube 55 is placed between the mount and proximal covering sheath 44, in order to secure the cells between proximal covering sheath 44 and the mount by filling any excess space between the mount and the proximal covering sheath. In some cases, in the absence of tube 55, proximal covering sheath 44 is prone to kinking during the insertion of device 20 into the subject's ascending aorta, due to there being excess space between the mount and the proximal covering sheath at these cells.

As described hereinabove, for some applications, device 20 includes projections 43 from the upstream end of the upstream anchor. For example, the projections may be T-shaped projections, as shown in FIGS. 3A-B. Typically, the upstream anchor is placed in close proximity to the subject's aortic valve. Therefore, the length of each of projections 43 is typically less than 8 mm, e.g., less than 3 mm, in order to avoid the projections causing trauma to the aortic valve leaflets. For some applications, each of the projections has a length of more than 0.5 mm, e.g., more than 1 mm. For example, the projections may have lengths of 0.5-8 mm, or 1-3 mm Typically, the upstream ends of the projections are configured to be atraumatic. For example, the upstream ends of the projections may be curved, as shown.

With reference to device 20 as shown in FIG. 5D, it is noted that since frame 52 of device 20 is shaped as a cylinder (with folded portions 56U and 56D being unfolded) during insertion of the device via the delivery device, device 20 has a relatively narrow profile. As such, the delivery device (e.g., catheter 42) typically has a diameter of 16 Fr or less, e.g. 12 Fr or less. By contrast, if device 20 was configured to define overlapping layers in its constrained configuration (e.g., by folded portions 56U and 56D being folded, even in the device's constrained configuration) then the profile of the device would be greater, and the diameter of the delivery device would be greater.

Referring again to FIG. 4D, as described hereinabove, for some applications, at the downstream end of downstream anchor 31, cells of frame 52 are not covered with material 54, but rather are open cells (as shown in FIG. 1B, for example). For some applications, the open cells at the downstream end of the downstream anchor protect the subject's brachiocephalic artery 53 from being occluded by the downstream anchor of the device, even in the event that the downstream anchor is placed in close proximity to the subject's brachiocephalic artery.

Figure 6A:
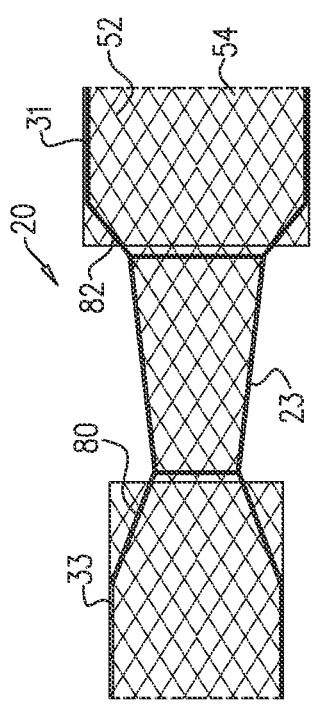
FIGS. 6A and 6B are schematic illustrations of a pressure-loss-reduction device for implanting inside a subject's ascending aorta, the device being constructed from modular components, in accordance with some applications of the present invention.
Figure 6B:
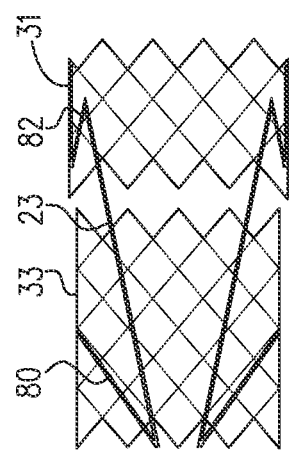

Reference is now made to FIGS. 6A and 6B, which are schematic illustrations of pressure-loss-reduction device 20, the device being made of a plurality of modular components, in accordance with some applications of the present invention. For some applications, device 20 is formed from a plurality of modular components of graft material. The graft material is typically formed from a combination of a metal or alloy frame 52 (e.g., a stent made of stainless steel or nitinol or cobalt chromium) and a covering material 54, e.g., a fabric and/or a polymer (such as expanded polytetrafluoroethylene (ePTFE), or woven, knitted and/or braided polyester), which is typically coupled to the inside of the frame via stitching, spray coating, encapsulation, electrospinning, dip molding and/or a different technique. In accordance with some applications, a layer of the material is coupled to the inside of at least a portion of the frame, the outside of at least a portion of the frame, and/or at least a portion of the frame is embedded within a layer of the material. For some applications, respective components are used to form (a) upstream anchor 33 configured to anchor and seal the device to the inner wall of the aorta at the upstream end of the device, (b) downstream anchor 31 configured to anchor and seal the device to the inner wall of the aorta at the downstream end of the device, and (c) an intermediate portion 23, inner surface 24 of which is configured to define conduit 26.

As shown, for some applications, at upstream and downstream ends of the intermediate portion, the covering material (e.g., the fabric) of the stent graft forms skirts 80, 82, which extend beyond the ends of the frame of the intermediate portion. The intermediate portion of the device is typically coupled to the upstream anchor 33 by stitching skirt 80 that extends from the upstream end of the intermediate portion to the upstream anchor, and is typically coupled to the downstream anchor 31 by stitching skirt 82 that extends from the downstream end of the intermediate portion to the downstream anchor. As shown in the transition from FIG. 6A to FIG. 6B, typically prior to being deployed within the subject's aorta, the upstream anchor and the downstream anchor are moved toward each other, such that (a) each of the upstream and downstream anchors overlaps with the intermediate portion, and (b) each of the skirts invert.

Figure 7A:
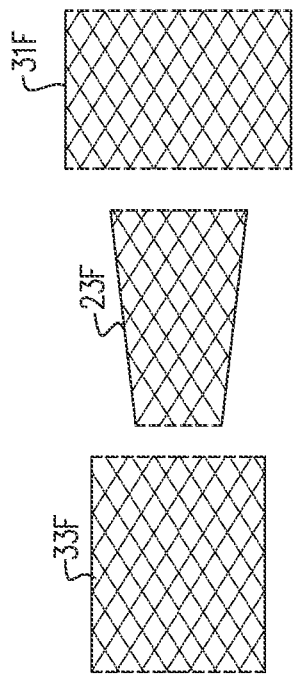
FIGS. 7A and 7B are schematic illustrations of a pressure-loss-reduction device for implanting inside a subject's ascending aorta, the device being constructed from modular components, in accordance with some alternative applications of the present invention.
Figure 7B:
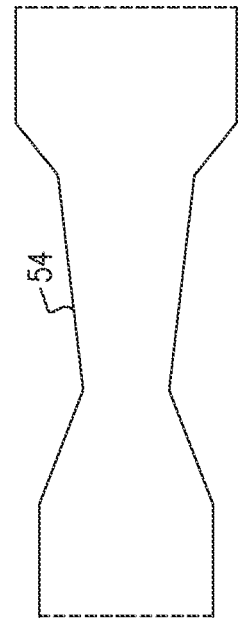

Reference is now made to FIGS. 7A and 7B, which are schematic illustrations of pressure-loss-reduction device 20, device 20 being made of a plurality of modular components, in accordance with some applications of the present invention. As described with reference to FIGS. 6A-B, for some applications, device 20 is formed from a plurality of modular components of graft material. The graft material is typically formed from a combination of a metal or alloy frame 52 (e.g., a stent made of stainless steel or nitinol or cobalt chromium) and a covering material 54, e.g., a fabric and/or a polymer (such as expanded polytetrafluoroethylene (ePTFE), or woven, knitted and/or braided polyester), which is typically coupled to the inside of the frame via stitching, spray coating, encapsulation, electrospinning, dip molding and/or a different technique. In accordance with some applications, a layer of the material is coupled to the inside of at least a portion of the frame, the outside of at least a portion of the frame, and/or at least a portion of the frame is embedded within a layer of the material. For some applications, respective components are used to form (a) frame portion 33F corresponding to upstream anchor 33 configured to anchor and seal the device to the inner wall of the aorta at the upstream end of the device, (b) frame portion 31F corresponding to downstream anchor 31 configured to anchor and seal the device to the inner wall of the aorta at the downstream end of the device, and (c) frame portion 23F corresponding to intermediate portion 23 of the device, inner surface 24 of which is configured to define conduit 26. For some applications, the frames are coupled to each other by a single piece of covering material (e.g., fabric) 54, which is shown in FIG. 7B, being coupled to the insides of the frame portions.

For some applications (not shown), a first modular frame component is used to define both downstream anchor 31 and intermediate portion 23, while a second separate modular frame component is used to define upstream anchor 33. For some such applications, the first and second modular frame components are coupled to each other via a skirt that extends from the upstream end of the first modular component, e.g., in the manner described with reference to FIGS. 6A-6B. For some such applications, the first and second modular frame components are coupled to each other via a single piece of covering material (e.g., fabric) 54, e.g., in the manner described with reference to FIGS. 7A-7B.

Figure 8A:
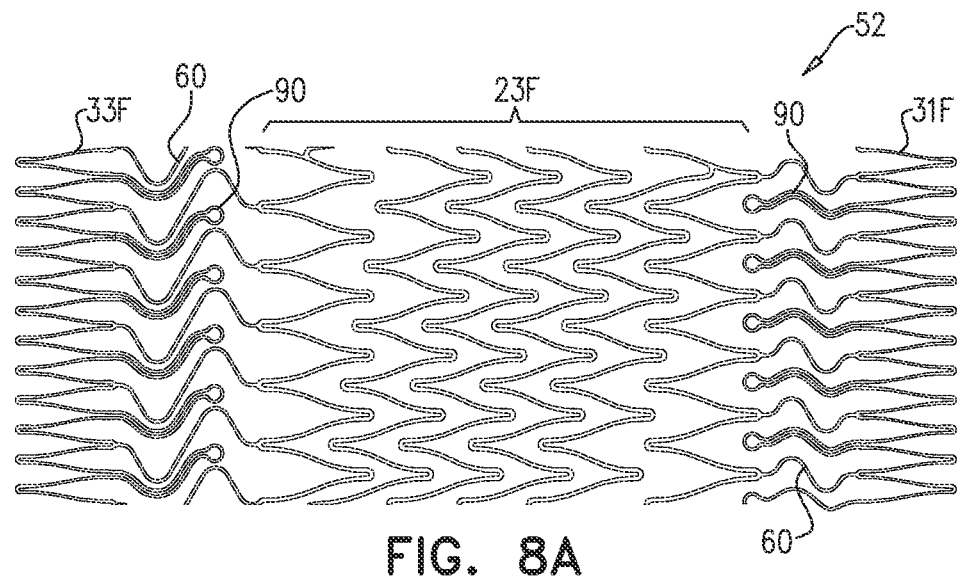
FIGS. 8A and 8B are schematic illustrations of a pressure-loss-reduction device for implanting inside a subject's ascending aorta, the device including anchor extensions on one or more anchors of the device, in accordance with some applications of the present invention
Figure 8B:
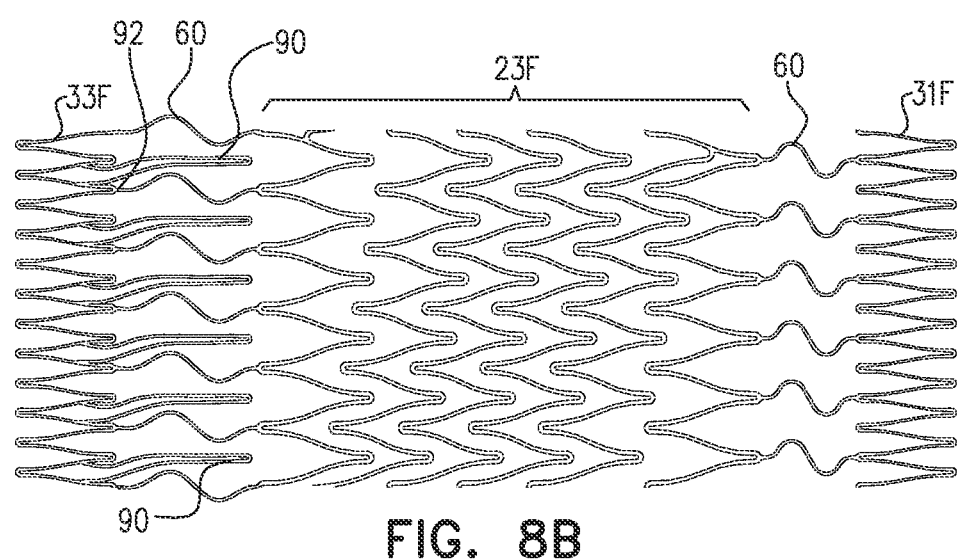

Reference is now made to FIGS. 8A and 8B, which are schematic illustrations of respective views of pressure-loss-reduction device 20, the device including anchor extensions 90 on one or more anchors of the device (e.g., upstream anchor 33 and/or downstream anchor 31), in accordance with some applications of the present invention. As described with reference to FIGS. 2A-C, FIGS. 8A and 8B shows a flattened profile of device frame 52, which depicts (for illustrative purposes) how the frame of the device would appear if, prior to shape setting the frame, a longitudinal incision was to be made along the length of the frame at a given circumferential location of the frame, and the frame were to then be laid out flat upon a surface. For some applications, the anchor extensions are sinusoidal, as shown in FIG. 8A. For some applications, the anchor extensions extend from both frame portion 33F that defines upstream anchor 33, and frame portion 31F that defines downstream anchor 31, again as shown in FIG. 8A. As described hereinabove, for some applications, at folded portions of the device the frame of the device defines sinusoidal struts 60. For some applications, the frame is cut from a tube of the metal or alloy, and sinusoidal anchor extensions are cut from tube at the same longitudinal portion of the tube as a portion of the frame that defines the sinusoidal struts. The sinusoidal anchor extensions are shape set, such that when the device is deployed within the subject's aorta, the sinusoidal anchor extensions exert an outward radial force upon the inner wall of the aorta, to thereby anchor the device within the aorta. For some applications, the sinusoidal shape of the anchor extensions provides the anchors with greater flexibility than if the anchors were formed from straight struts.

For some applications, sinusoidal struts 60 that form upstream folded portion 56U of device 20 are configured to extend from inter-strut junctions 92 of portion 33F of the frame that corresponds to upstream anchor 33. For some applications anchor extensions 90 extend from struts of portion 33F of the frame, between the inter-strut junctions, as shown in FIG. 8B. As described with reference to FIG. 8A, the anchor extensions are shape set, such that when the device is deployed within the subject's aorta, the anchor extensions exert an outward radial force upon the inner wall of the aorta, to thereby anchor the device within the aorta.

Figure 9:
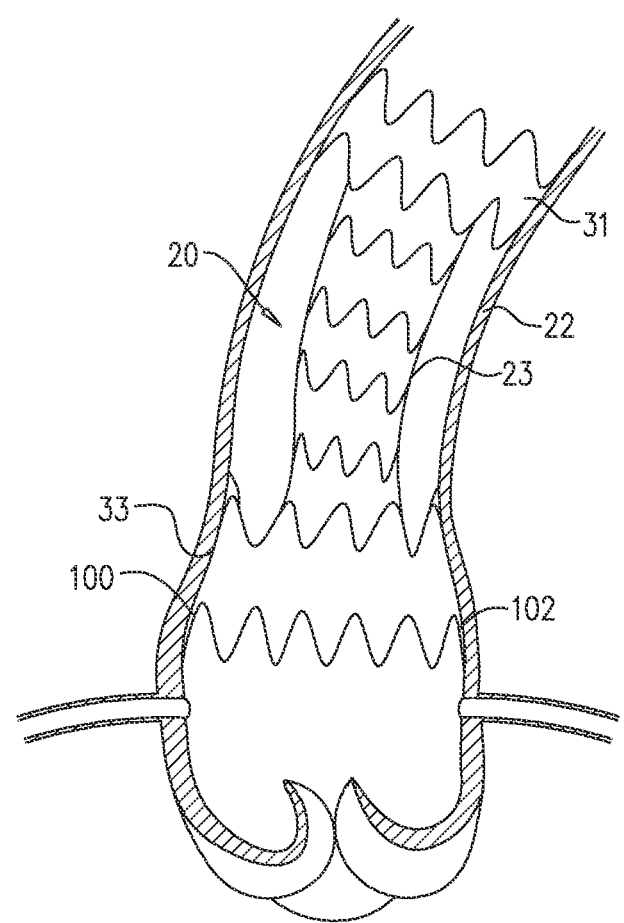
FIG. 9 is a schematic illustration of a pressure-loss-reduction device for implanting inside a subject's ascending aorta, an upstream anchor of the device being shaped to define a flared upstream skirt, in accordance with some applications of the present invention.

Reference is now made to FIG. 9, which is a schematic illustration of pressure-loss-reduction device 20, upstream anchor 33 of the device being shaped to define a flared upstream skirt 100, in accordance with some applications of the present invention. For some applications, the flared upstream skirt is configured to become deployed within the subject's aortic sinuses 102. The flared skirt typically acts as a further anchoring mechanism that prevents device 20 from migrating in the downstream direction. For some applications, the flared skirt is configured to exert an outward normal force upon the inner wall of the aortic sinuses. For some applications, the flared skirt is covered with covering material 54 (e.g., a fabric such as expanded polytetrafluoroethylene (ePTFE) or woven polyester, as described hereinabove). Alternatively, the flared skirt comprises frame 52 (which as described hereinabove is typically a metal or an alloy (e.g., stainless steel or nitinol)), and the frame is not covered with a covering material (e.g., fabric).

Figure 10A:
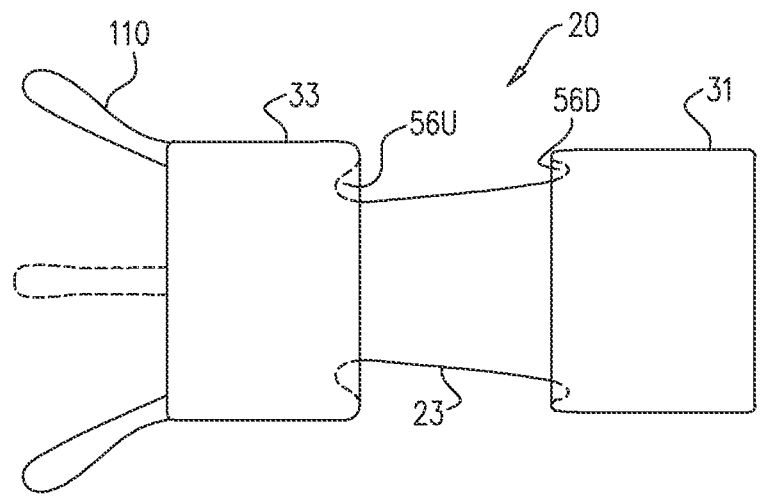
FIGS. 10A and 10B are schematic illustrations of a pressure-loss-reduction device for implanting inside a subject's ascending aorta, the device including a plurality of anchor extensions extending from its upstream anchor, which are configured to become anchored within respective aortic sinuses of the subject's aorta, in accordance with some applications of the present invention.
Figure 10B:
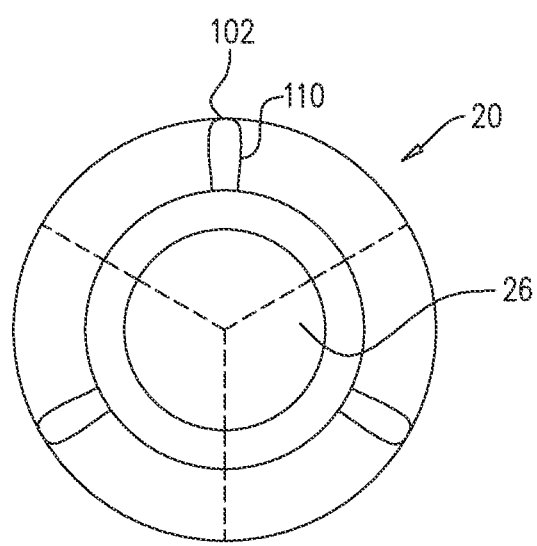

Reference is now made to FIGS. 10A and 10B, which are schematic illustrations of respective views of pressure-loss reduction device 20, the device including a plurality of (e.g., three) anchors 110 extending from an upstream end of upstream anchor 33, in accordance with some applications of the present invention. (In the slice view shown in FIG. 10A, one of the anchors is shown with dashed lines, to indicate that in this cross-sectional via of the device, this anchor wouldn't normally be visible. However, the anchor is added in dashed lines for illustrative purposes.) For some applications, anchors 110 are configured to become anchored within respective aortic sinuses of the subject's aorta. The anchors typically act as a further anchoring mechanism that prevents device 20 from migrating in the downstream direction. For some applications, the anchors are to configured exert an outward normal force upon the inner wall of the aortic sinuses. FIG. 10B shows a view of the device from underneath the aortic valve, with the commissures of the aortic valve being indicated by dashed lines.

Figure 11A:
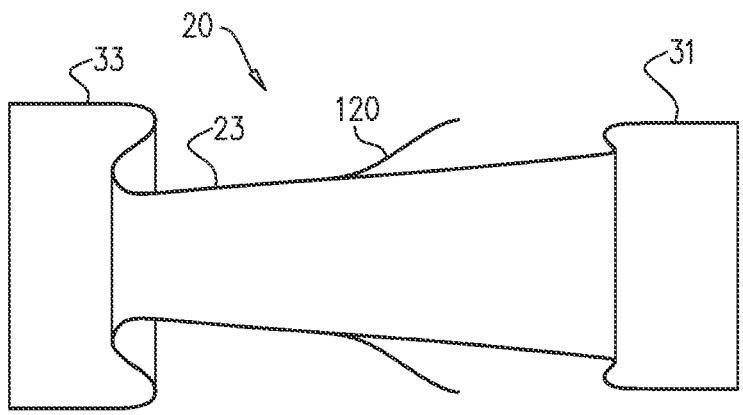
FIGS. 11A, 11B, and 11C are schematic illustrations of a pressure-loss-reduction device for implanting inside a subject's ascending aorta, a plurality of centralizing anchors extending from an intermediate portion the device, in accordance with some applications of the present invention.
Figure 11B:
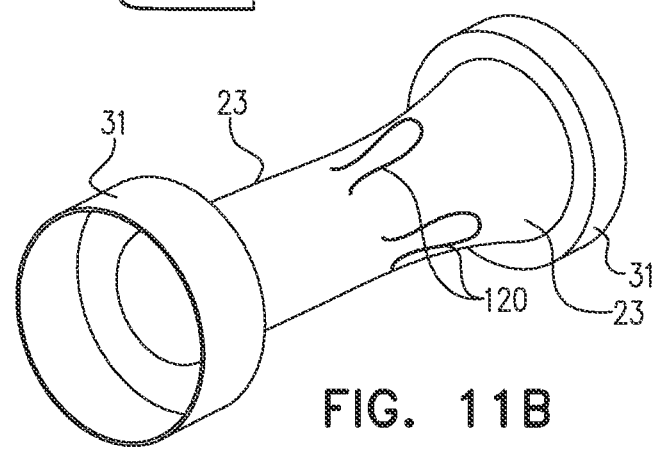
Figure 11C:
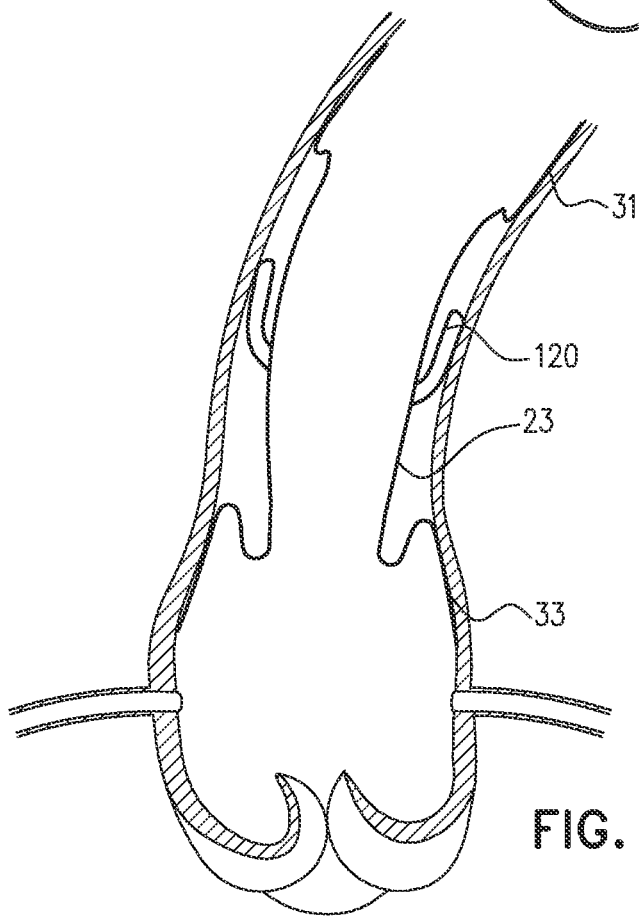

Reference is now made to FIGS. 11A, 11B, and 11C, which are schematic illustrations of pressure-loss-reduction device 20, one or more centralizing anchors 120 extending from intermediate portion 23 of the device (which has inner surface 24, which defines conduit 26), in accordance with some applications of the present invention. The one or more centralizing anchors are configured to extend from the intermediate portion of the device to the inner wall of the subject's aorta, and (a) to thereby assist in anchoring the device within the aorta, and/or (b) to centralize the conduit with respect to the longitudinal axis of the aorta. FIG. 11A shows a slice view of the device, FIG. 11B shows a three-dimensional view of the device, and FIG. 11C shows a cross-sectional view of the device deployed within the subject's aorta, downstream of the aortic valve. Typically, the anchors comprise extensions of the frame that extend from portion 23F of the frame. Further typically, as shown material 54 defines a continuous surface along conduit 26, even at the location from which the centralizing anchors extend.

Figure 12A:
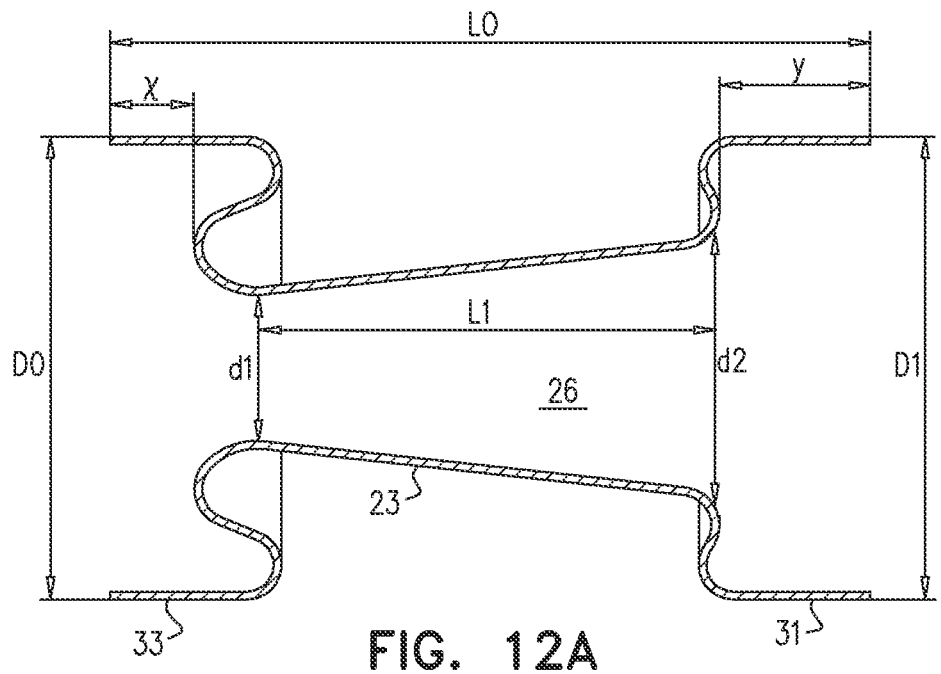
FIGS. 12A, 12B, and 12C are schematic illustrations of a pressure-loss-reduction device for implanting inside a subject's ascending aorta, in accordance with some applications of the present invention.
Figure 12B:
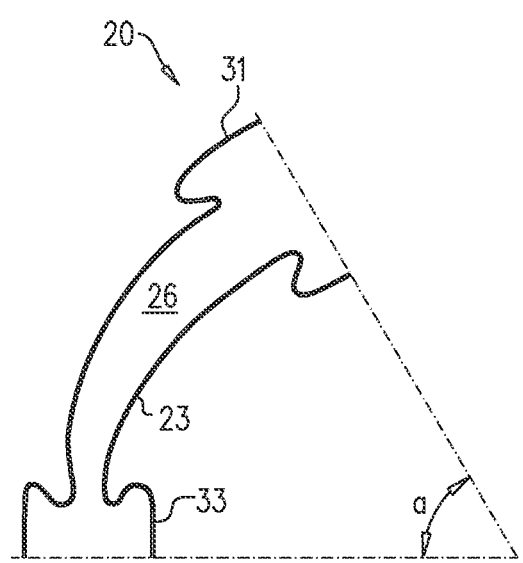
Figure 12C:
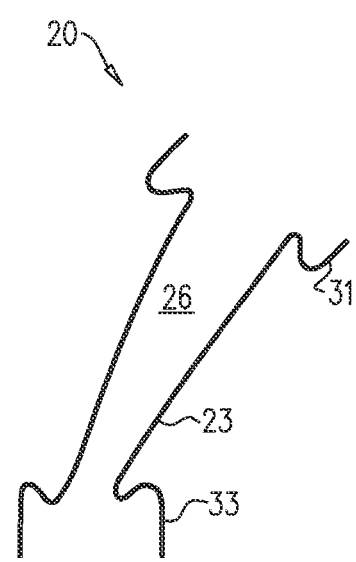

Reference is now made to FIGS. 12A, 12B, and 12C, which are schematic illustrations of pressure-loss-reduction device 20, in accordance with some applications of the present invention. Referring to device 20 as schematically illustrated in FIGS. 12A, 12B, and 12C, device 20 typically has the following dimensions, when in a non-constrained configuration:

A distance x from the upstream end of the upstream anchor to an upstream end of conduit 26 is typically less than 15 mm, e.g. less than 10 mm. For some applications, the upstream end of the conduit extends beyond the upstream end of the upstream anchor by a distance of up to 5 mm.

A distance y from the downstream end of the downstream anchor to a downstream end of conduit 26 is typically less than 30 mm, e.g. less than 15 mm.

A diameter d1 of conduit 26 at an upstream end of the diverging portion is typically more than 10 mm (e.g., more than 12 mm), and/or less than 20 mm (e.g., less than 16 mm), e.g., between 10 and 20 mm, or between 12 and 16 mm.

A diameter d2 of conduit 26 at a downstream end of the diverging portion is typically more than 12 mm (e.g., more than 16 mm), and/or less than 30 mm (e.g., less than 25 mm), e.g., between 12 and 30 mm, or between 16 and 25 mm.

Diameter D0 of upstream anchor 33 is typically more than 20 mm (e.g., more than 23 mm), and/or less than 45 mm (e.g., less than 36 mm), e.g., between 20 and 45 mm, or between 23 and 36 mm.

Diameter D1 of downstream anchor 31 is typically more than 20 mm (e.g., more than 26 mm), and/or less than 48 mm (e.g., less than 42 mm), e.g., between 20 and 48 mm, or between 26 and 42 mm.

An angle a between a plane defined by an upstream end of the upstream anchor and a plane defined by the downstream end of the downstream anchor is between 0 and 120 degrees, or between 30 and 90 degrees.

Typically, a length L0 of pressure-loss-reduction device 20 is greater than 20 mm (e.g., greater than 30 mm), and/or less than 90 mm (e.g., less than 60 mm), e.g., 20-90 mm, or 30-60 mm. For some applications, a length L1 of the diverging portion of conduit 26 (measured along the longitudinal axis of the device) is greater than 20 mm (e.g., greater than 30 mm), and/or less than 70 mm (e.g., less than 60 mm), e.g., 20-70 mm, or 30-60 mm, and length L0 of the device is greater than the length of the diverging portion. As described hereinabove, typically, the conduit is divergent over more than 50 percent, e.g., more than 75 percent, or more than 90 percent of the total length of the conduit (i.e., the diverging portion of the conduit comprises more than 50 percent, e.g., more than 75 percent, or more than 90 percent of the total length of the conduit). Further typically, the conduit is divergent over more than 50 percent, e.g., more than 75 percent, or more than 90 percent of the total length of the device (i.e., the diverging portion of the conduit comprises more than 50 percent, e.g., more than 75 percent, or more than 90 percent of the total length of the conduit).

For some applications, a ratio of (a) outer diameter D0 of upstream anchor 33 to (b) outer diameter D1 of the distal end of downstream anchor 31 is greater than 3:4, and/or less than 4:3, e.g., between 3:4 and 4:3. Outer diameter D0 of the upstream anchor is typically made to conform with the inner diameter of the subject's aorta toward the upstream end of the device, and outer diameter D1 of the downstream anchor is typically made to conform with the inner diameter of the subject's aorta at the downstream end of the device. Since there is some variation in the shapes and sizes of subject's aortas, the ratio of D0:D1 typically varies between 3:4 and 4:3. Typically, the maximum outer diameter of the device (i.e., the outer diameter of the device at the location along the length of the device at which the outer diameter is at its maximum) is greater than 18 mm (e.g., greater than 25 mm), and/or less than 45 mm (e.g., less than 35 mm), e.g., 18-45 mm, or 25-35 mm.

Further typically, the difference between diameter d1 of conduit 26 at an upstream end of the diverging portion, and diameter d2 of conduit 26 at a downstream end of the diverging portion is greater than 3 mm (e.g., greater than 5 mm, or greater than 10 mm), and/or less than 30 mm (e.g., less than 20 mm), e.g., 5-30 mm, or 10-20 mm. For some applications, the ratio of diameter d2 of conduit 26 at a downstream end of the diverging portion to diameter d1 of conduit 26 at an upstream end of the diverging portion is greater than 4:3 (e.g., greater than 2:1), and/or less than 4:1 (e.g., less than 3:1), e.g., 4:3-4:1, or 2:1-3:1. It is noted that the cross-section of the conduit is not necessarily circular. For applications in which the term "diameter" is used with reference to an object or a portion of an object having a non-circular cross-section, the term "diameter" should be interpreted as meaning the hydraulic diameter, i.e. 4A/P (where A is the cross-sectional area, and P is the perimeter).

For some applications, the ratio of diameter d2 of conduit 26 at a downstream end of the diverging portion to diameter d1 of conduit 26 at an upstream end of the diverging portion is less than 4:3, for example between 5:4 and 7:6 (e.g., 6:5). For some such applications, the difference between diameter d2 and diameter d1 is less than 3 mm, or less than 2 mm By way of example, d2 may be 14.5 mm and d1 may be 13 mm. It is noted that, even with devices with diameters d2 and d1 as described in the present paragraph, the inventors of the present application have found that some of the beneficial results of placing the device in the aorta of a subject with aortic valve stenosis are likely to be achieved, based upon in vitro experiments that were performed with such devices using a model of the aortic valve and the ascending aorta with a pulse generator. Moreover, the inventors of the present application have found that some of the beneficial results of placing the device in the aorta of a subject with aortic valve stenosis are likely to be achieved even with a device in which conduit 26 does not diverge, but is cylindrical, based upon in vitro experiments that were performed with such devices using a model of the aortic valve and the ascending aorta with a pulse generator. Therefore, the scope of the present invention includes pressure-loss-reduction device 20 that is generally as described with reference to FIGS. 1A-B, but in which conduit 26 does not diverge, but is cylindrical, and methods of use of such a device, mutatis mutandis, as described in further detail hereinbelow with reference to FIG. 13B. For some applications (not shown), rather than the diameter of the diverging portion increasing in a gradual manner, the diameter of the diverging portion increases in a stepwise manner.

For some applications, even in the non-constrained configuration of the device (i.e., in the absence of any external forces being exerted upon the device) intermediate portion 23 of the device (which has inner surface 24 that defines conduit 26) is configured to be curved along the longitudinal axis of the conduit, as shown in FIG. 12B. Alternatively, as shown in FIG. 12C, in the non-constrained configuration of the device, intermediate portion 23 of the device (which has inner surface 24 that defines conduit 26) is configured to be disposed at an angle with respect to upstream anchor 33 (i.e., such that the longitudinal axis of the conduit forms an angle with respect to the longitudinal axis of the upstream anchor), but the conduit is not curved. For some applications, the device as shown in FIG. 12C is configured such that the conduit become curved upon being placed in the ascending aorta, such as to conform to the curvature of the ascending aorta.

It is noted that, typically, the dimensions of device 20 described herein are the dimensions that the device is configured to have, when the device is in a non-constrained configuration. Typically, if the device is inserted via a delivery device, such as catheter 42 (e.g., as described with reference to FIGS. 4A-5D), the device is constrained during its insertion, such that the dimensions of the device during the insertion may not be as described herein. Further typically, upon being released from the delivery device inside the aorta, device 20 assumes a configuration that is somewhat constrained by the aorta. For some applications, device 20 is configured such that in its non-constrained configuration at least a portion of the conduit 26 diverges, but the conduit 26 is not curved, as shown in FIG. 1B. For some such applications, conduit 26 of device 20 is configured to become curved upon being deployed in the aorta, by virtue of forces exerted upon the device by the inner wall of the aorta. Typically, portion 23F of the frame (corresponding to intermediate portion 23 of the device) is configured to be flexible in order to facilitate curving of the intermediate portion of the device upon being placed inside the aorta, e.g., using techniques as described hereinabove with reference to FIGS. 2A-C.

For some applications, pressure-loss-reduction device 20 is implanted in a non-minimally-invasive manner (e.g., using traditional surgical techniques). For some such applications, even during the insertion of the device, the device is configured in its non-constrained configuration.

As described hereinabove, typically, pressure-loss-reduction device 20 is made of graft material, which is typically formed from a combination of frame 52, which is typically a metal or alloy frame (e.g., a stent made of stainless steel or nitinol or cobalt chromium), and covering material 54, e.g., a fabric and/or a polymer (such as expanded polytetrafluoroethylene (ePTFE), or woven, knitted and/or braided polyester), which is typically coupled to the frame via stitching, spray coating, encapsulation, electrospinning, dip molding and/or a different technique. Typically, the covering material covers the inside of at least a portion of frame 52, such that blood flowing through the device contacts the material. Alternatively or additionally, the covering material is disposed outside at least a portion of the frame, for example, in order to facilitate retraction of the device back into a delivery device. For example, a first layer of covering material may be disposed inside the frame, and a second layer of the material may be disposed outside the frame. For some applications, at least a portion of the frame is embedded by the material.

Figure 13A:
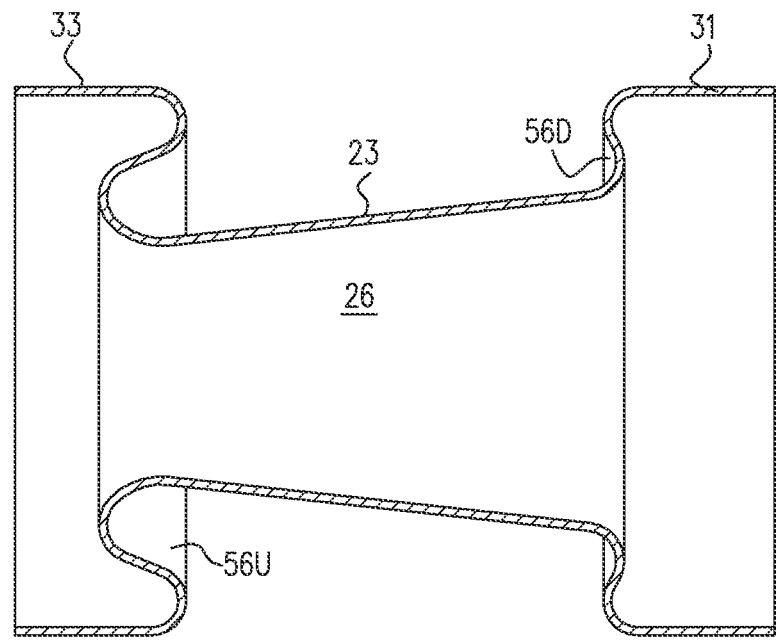
FIG. 13A is a schematic illustration of a pressure-loss-reduction device for implanting inside a subject's ascending aorta, the device including a non-curved, diverging inner conduit in a non-constrained configuration of the device, in accordance with some applications of the present invention.
Figure 13B:
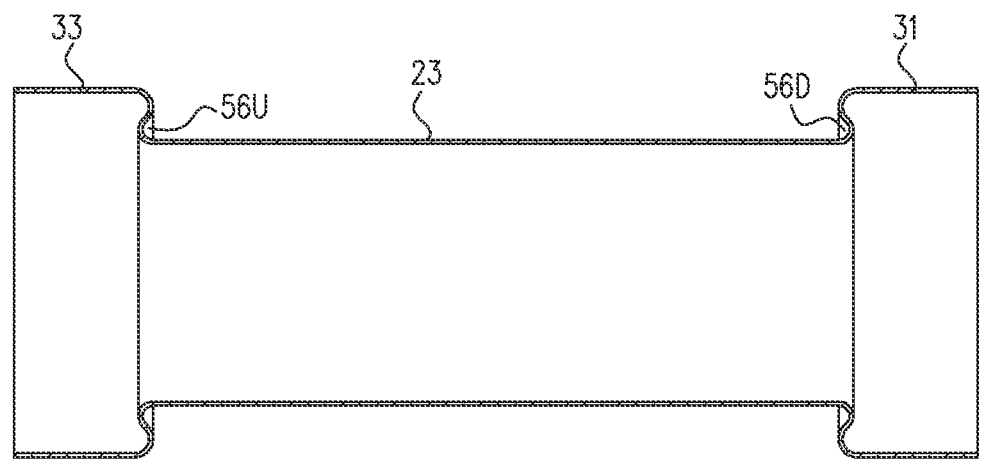
FIG. 13B is a schematic illustration of a pressure-loss-reduction device for implanting inside a subject's ascending aorta, the device including a generally cylindrical inner conduit in a non-constrained configuration of the device, in accordance with some applications of the present invention.

Reference is now made to FIG. 13A, which is a schematic illustration of a pressure-loss-reduction device 20 for implanting inside a subject's aorta, conduit 26 of the device being configured to be non-curved and diverging, in a non-constrained configuration of the device, in accordance with some applications of the present invention. Reference is also made to FIG. 13B, which is a schematic illustration of pressure-loss-reduction device 20 for implanting inside a subject's aorta, conduit 26 of the device being configured to be non-curved and cylindrical (i.e., non-diverging) in a non-constrained configuration of the device, in accordance with some applications of the present invention. Apart from the shapes of the conduit, device 20 as shown in FIGS. 13A and 13B is generally similar to that shown in, and described with respect to, FIGS. 1A and 1B. Thus, device 20 typically includes upstream anchor 33, downstream anchor 31, and folded portions 56U and 56D, which are disposed between intermediate portion 23 (inner surface 24 of which defines conduit 26), the portions all being generally as described hereinabove.

With reference to FIG. 13B, it is noted the inventors of the present application have found that some of the beneficial results of placing device 20 in the aorta of a subject with aortic valve stenosis are likely to be achieved even if the conduit is not configured with dimensions as described with reference to FIGS. 12A-C (based upon in vitro experiments that were performed with such devices using a model of the aortic valve and the ascending aorta with a pulse generator). Moreover, the inventors of the present application have found that some of the beneficial results of placing the device in the aorta of a subject with aortic valve stenosis are likely to be achieved even with a device in which conduit 26 does not diverge but is cylindrical (again based upon in vitro experiments that were performed with such devices using a model of the aortic valve and the ascending aorta with a pulse generator). Therefore, the scope of the present invention includes pressure-loss-reduction device 20 that is generally as described with reference to FIGS. 1A-B, but in which conduit 26 does not diverge but is cylindrical, and methods of use of such a device, mutatis mutandis.

It is noted that the device as shown in FIG. 13B may be used in applications other than as a pressure-loss reduction device for placement in a subject's aorta. For example, the device as shown in FIG. 13B may be used as a stent graft in order to repair an aneurysm. Alternatively or additionally, device 20 may be configured to function as a stent, and/or a bio-absorbable stent. Moreover, in general, any one of the embodiments of device 20 described herein may be used in applications other than as a pressure-loss reduction device for placement in a subject's aorta, e.g., as a stent graft, a stent, and/or a bio-absorbable stent.

Figure 14A:
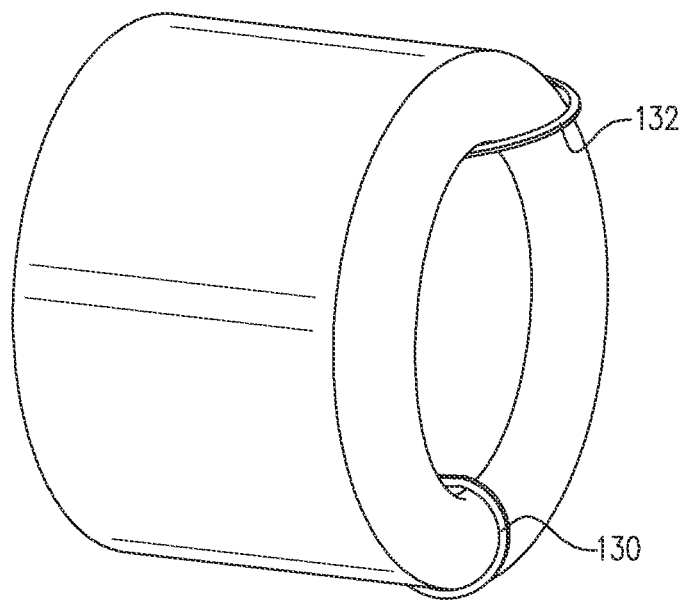
FIG. 14A is a schematic illustration of a straight strut and a portion of a sinusoidal strut that are shown in folded configurations, in order to illustrate a concept that is utilized in accordance with some applications of the present invention.

Reference is now made to FIG. 14A, which is a schematic illustration of a straight strut 130 and a portion of a sinusoidal strut 132 that are shown in folded configurations, in order to illustrate a concept that is utilized in accordance with some applications of the present invention. As described hereinabove, typically the portions of frame 52 that correspond to upstream folded portion 56U and downstream folded portion 56D are configured as described with reference to FIGS. 2A-C, with struts 60 at the folded portions being shaped sinusoidally. A straight strut, such as strut 130 that is simply folded to form a folded portion can only be folded to a fold having a certain minimum radius of curvature, before the strut will undergo plastic deformation and/or fracture. A sinusoidal strut, such as strut 132, that is folded to form a sinusoidal folded portion, in accordance with some applications of the present invention, undergoes the fold along a diagonal path. Therefore, the fold is spread over a longer distance, and the sinusoidal strut can be folded to a fold having a smaller radius of curvature, before the strut undergoes plastic deformation and/or fracture. Moreover, the sinusoidal strut, also undergoes torsion, which allows the strut to be folded to a smaller radius of curvature, ceteris paribus.

Figure 14B:
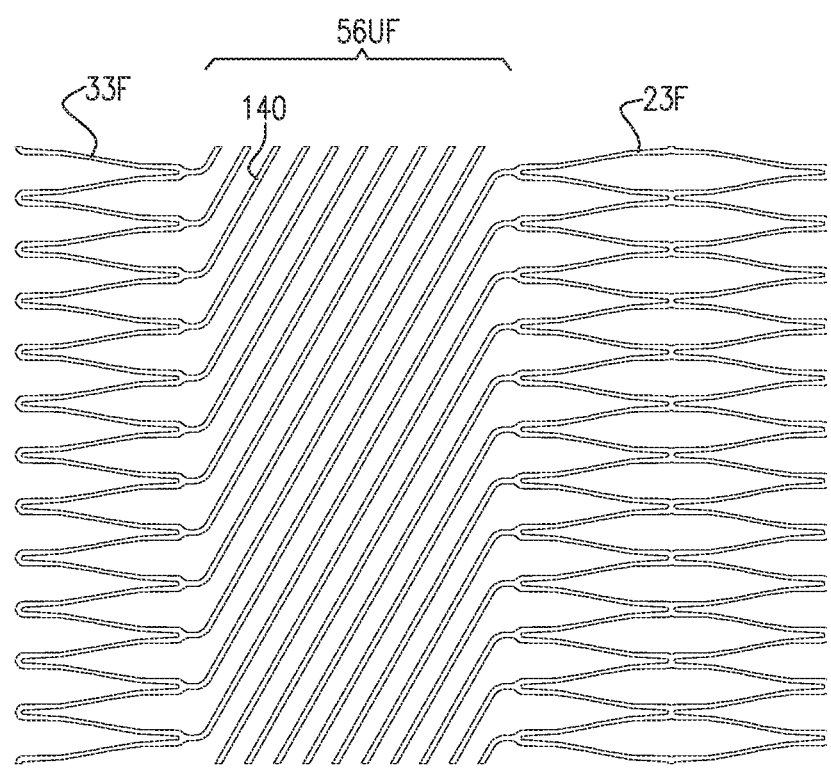
FIG. 14B is a schematic illustration of a portion of a frame of a pressure-loss-reduction device for implanting inside a subject's ascending aorta, the portion including a plurality of diagonal struts that are configured to facilitate folding of the portion of the frame, in accordance with some applications of the present invention.

Reference is now made to FIG. 14B, which is a schematic illustration of a portion of frame 52 of pressure-loss-reduction device 20 for implanting inside a subject's aorta, the portion including a plurality of straight, angled struts 140 that are configured to facilitate folding of folded portion 56U and/or 56D of the frame, in accordance with some applications of the present invention. FIG. 14B shows (for illustrative purposes) a flattened profile of the portion of the frame, which depicts how the portion of the frame of the device would appear if, prior to shape setting the frame, a longitudinal incision was to be made along the length of the frame at a given circumferential location of the frame, and the frame were to then be laid out flat upon a surface. As shown, for some applications, portion 56UF of the frame (corresponding to folded portion 56U of device 20), the frame defines a plurality of straight struts 140, which are disposed parallel to each other, and at an angle (e.g., an angle of between 20 degrees and 70 degrees) with respect to the length of the frame. Typically, the folded portions are formed by shape setting. For some applications, the straight struts facilitate shape setting the frame of device 20 to include folded portion 56U, such that the radius of curvature of the curve made by the folded portion is smaller than if the folded portion were to be formed solely by shape setting a straight strut. For some applications, the folded portion can thereby be longer, such as to enhance sealing with respect to the aorta that is provided by the folded portion, as described hereinabove. For some applications, allowing upstream folded portion 56U to be longer facilitates placement of the upstream end of the conduit closer to the orifice of the aortic valve, by allowing greater overlap between the conduit and the upstream anchor. For some applications, similar techniques are used for downstream folded portion 56D.

For some applications (not shown), at the portion of frame 52 corresponding to folded portion 56U and/or 56D, the frame defines struts which form closed cells, like at other locations of the frame. Typically, for such applications, the cells that are disposed at the portion of frame 52 corresponding to folded portion 56U and/or 56D are larger than the cells at other locations of the frame, in order to facilitate shape setting the frame of device 20 to include folded portion 56U and/or 56D, such that the folded portion can encompass a smaller radius of curvature relative if the folded portion were to be formed solely via the shape-setting process.

Figure 15:
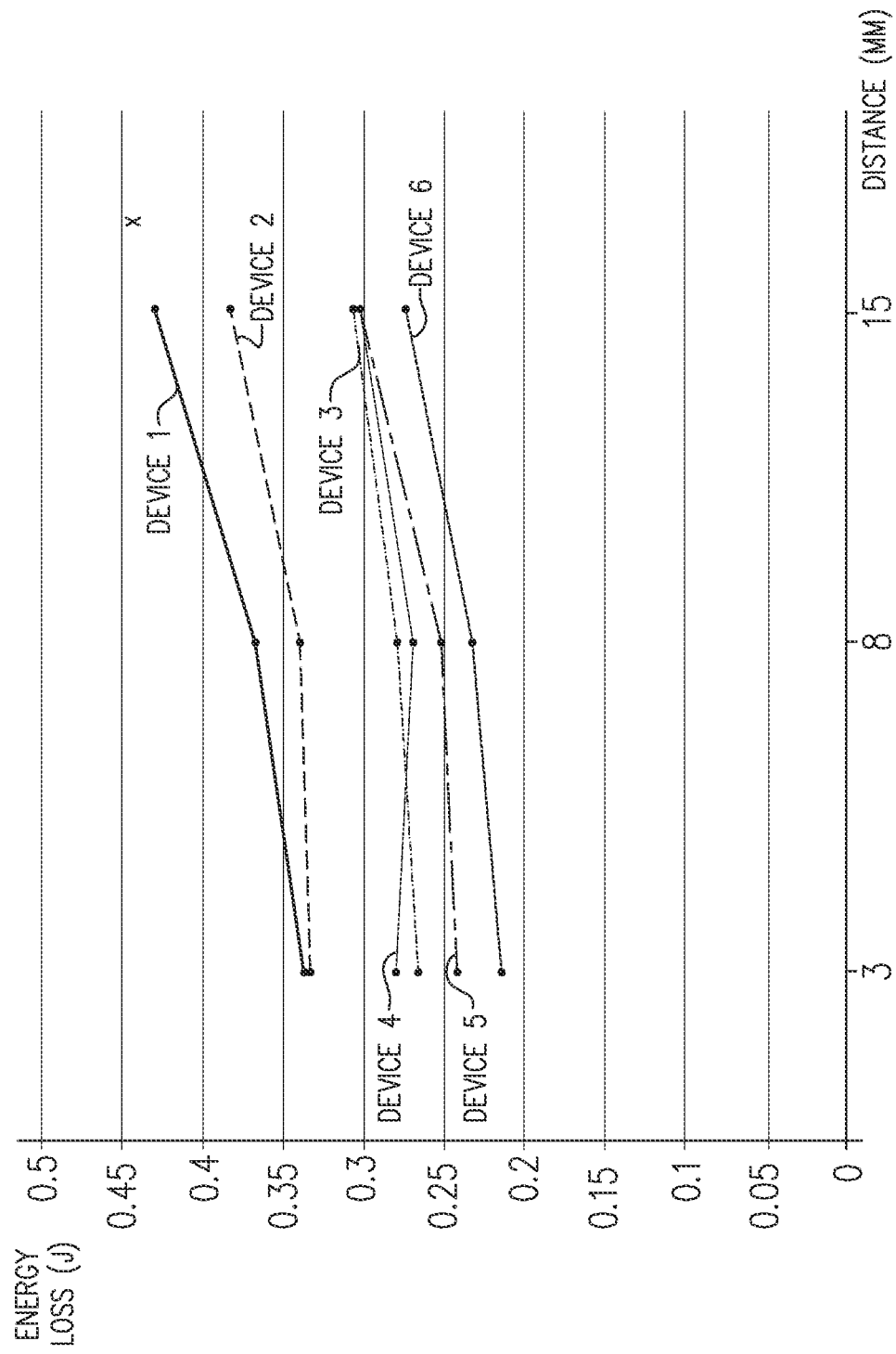
FIG. 15 is a graph showing results of an experiment that was performed, in accordance with some applications of the present invention.

Reference is now made to FIG. 15, which is a graph showing results of an experiment that was performed, in accordance with some applications of the present invention. A model of an aorta with a stenosed aortic valve was made using a pipe having a diameter of 27 mm, and a surgical bioprosthetic valve that was sewn to mimic severe aortic stenosis. Flow was measured using a first flow sensor disposed at an upstream location directly upstream of the valve, and a second flow sensor that was placed at a downstream location, at a location sufficiently downstream of the valve that the flow had lost a substantial amount of its pulsatility. Similarly, pressure was measured using a first pressure sensor disposed at the upstream location upstream of the valve (and therefore measuring pressure that is representative of ventricular pressure), and a second pressure sensor that was placed at the downstream location, downstream of the valve (and therefore measuring pressure that is representative of pressure in the aorta, downstream of the aortic valve). Flow and pressure were measured during pulsatile flow, the pulsatile flow being generated by a pulse duplicator system manufactured by LifeTec Group™. A compliant tube was placed downstream of the second pressure sensor and upstream of the second flow sensor, the compliance of the tube being such as to mimic the compliance of an aorta that has a systolic blood pressure of 120 mmHg, and a diastolic blood pressure of 80 mmHg.

Energy loss per pulse, between the upstream location and the downstream location, was calculated using the following equation:

$$E_{Loss} = \int_{t1}^{t2} Q(t) * \Delta P(t) dt$$

where Q is flow calculated based upon a combination of the flow measurements that were performed by the first and second flow sensors, and $\Delta P$ is the difference between the pressure measured by the second sensor and the pressure measured by the first pressure sensor.

Energy loss was calculated (a) when no device was placed between the valve and the downstream location, and (b) when various devices having diverging conduits as described herein were placed between the valve and the downstream location. The devices had the following characteristics:

Device 1—Length of diverging portion of the conduit 25 mm, diameter of conduit at upstream end of diverging portion 11.5 mm.

Device 2—Length of diverging portion of the conduit 25 mm, diameter of conduit at upstream end of diverging portion 13 mm.

Device 3—Length of diverging portion of the conduit 50 mm, diameter of conduit at upstream end of diverging portion 11.5 mm.

Device 4—Length of diverging portion of the conduit 25 mm, diameter of conduit at upstream end of diverging portion 14 mm.

Device 5—Length of diverging portion of the conduit 50 mm, diameter of conduit at upstream end of diverging portion 13 mm.

Device 6—Length of diverging portion of the conduit 50 mm, diameter of conduit at upstream end of diverging portion 14 mm.

For the energy loss measurements that were performed for when the devices were placed between the valve and the downstream location, each of the devices was placed such that the upstream end of the conduit of the device was at various distances from the valve, and the energy loss was calculated for the respective devices at the respective distances from the valve.

The energy loss per pulse when no device was placed between the valve and the downstream location was approximately 0.44 Joules per pulse, indicated by the "x" in the upper right of the graph. The energy loss per pulse for the respective devices is shown in the curves of the graph. It may be observed that (a) placing a device as described herein between the valve and the downstream location reduces energy loss, and (b) in general, the closer that the upstream end of the conduit of the device is to the valve, the lower the energy loss. Therefore, as described hereinabove, in accordance with some applications of the present invention, device 20 includes a folded portion at its upstream end, as described hereinabove. The folded portion facilitates placement of the device within the ascending aorta such that (a) the upstream anchor is placed sufficiently far from the aortic valve such that the anchor does not impede blood flow to the coronary arteries, but (b) the upstream end of the device's conduit is close to the aortic valve orifice.

For some applications, using the apparatus and methods described herein, device 20 is implanted such that the upstream end of upstream anchor 33 is deployed within 5 mm of the subject's sinotubular junction, either upstream of the subject's sinotubular junction, or downstream of the subject's sinotubular junction. For some applications, device 20 is implanted such that the upstream end of conduit 26 is deployed within 25 mm of the subject's aortic valve orifice.

It is noted that, although device 20 is generally described herein as being implanted in the subject's aorta (e.g., ascending aorta), the scope of the present invention includes placing device 20 inside a longitudinal portion of any blood vessel of a subject, such that the device causes blood to flow in an antegrade direction through conduit 26, and such that, within the longitudinal portion in which the device is placed, blood flow via any flow-path other than through the conduit is prevented by the deployment of the device within the portion.

The terms "proximal" and "distal" are generally used in the present application to refer to the location of the respective elements in the aorta with respect to the aortic valve. That is, the term "proximal" refers to an element that is "upstream" and closer to the aortic valve, and the term "distal" refers to an element that is "downstream" and further from the aortic valve. Thus, the term "proximal" is used synonymously with the term "upstream" and the term "distal" is used synonymously with the term "downstream." In cases in which the device is placed in a different position within the subject's body, the terms "proximal" and "distal" are to be understood with respect to the direction of blood flow, a location that is relatively upstream being considered "proximal" and a location that is relatively downstream being considered "distal." It is noted that when used with reference to catheter 42, the term "distal" is used to refer to the end of the catheter that is inserted the furthest into the subject's body.

Inventive concept 1. Apparatus for use with a delivery device, comprising:
an implantable device having a proximal end and a distal end, the implantable device being configured:
to be inserted into a blood vessel of a subject while the implantable device is disposed inside the delivery device and is constrained in a constrained configuration by the delivery device,
to assume a non-constrained configuration inside the blood vessel by being released from the delivery device,
in its constrained configuration, to define a tube having an inner surface and an outer surface, and
to assume its non-constrained configuration, by:
the proximal end of the implantable device radially expanding such that a proximal portion of the outer surface of the implantable device contacts an inner wall of the blood vessel,
an intermediate portion of the implantable device radially expanding such that along the intermediate portion of the implantable device, the inner surface defines a conduit that extends through the implantable device,
the distal end of the implantable device radially expanding such that a distal portion of the outer surface contacts the inner wall of the blood vessel,
the implantable device forming a first folded portion between the proximal end of the implantable device and the intermediate portion of the implantable device, such that along a longitudinal direction of the implantable device, there is partial overlap between the proximal portion of the outer surface of the implantable device and the intermediate portion of the implantable device, and
the implantable device forming a second folded portion between the distal end of the implantable device and the intermediate portion of the implantable device, such that along a longitudinal direction of the implantable device, there is partial overlap between the distal portion of the outer surface of the implantable device and the intermediate portion of the implantable device.

Inventive concept 2. Apparatus configured to be placed at least partially in an ascending aorta of a subject, the apparatus comprising:
an implantable device comprising:
an upstream anchor configured to anchor an upstream end of the device to an inner wall of the aorta;

a downstream anchor configured to anchor a downstream end of the device to the inner wall of the aorta; and an intermediate portion disposed at least partially between the upstream anchor and the downstream anchor, and configured to define a conduit through the device, the conduit being configured, when disposed within the ascending aorta:

to define a diverging portion that diverges in a direction from a proximal end of the conduit to a distal end of the conduit, such that a cross-sectional area of the diverging portion of the conduit at its distal end is greater than the cross-sectional area of the diverging portion of the conduit at its proximal end, and to define a curved longitudinal axis, such as to conform with curvature of the ascending aorta.

Inventive concept 3. The apparatus according to inventive concept 2, wherein the implantable device is configured, when disposed within the ascending aorta, to define a folded portion between the upstream anchor and the intermediate portion of the implantable device, such that along a longitudinal direction of the implantable device, there is partial overlap between the upstream anchor and the intermediate portion of the implantable device.

Inventive concept 4. The apparatus according to inventive concept 2, wherein the implantable device is configured, when disposed within the ascending aorta, to define a folded portion between the downstream anchor of the implantable device and the intermediate portion of the implantable device, such that along a longitudinal direction of the implantable device, there is partial overlap between the downstream anchor and the intermediate portion of the implantable device.

Inventive concept 5. The apparatus according to inventive concept 2, wherein the implantable device is configured, when disposed within the ascending aorta, to define:

a first folded portion between the upstream anchor and the intermediate portion of the implantable device, such that along a longitudinal direction of the implantable device, there is partial overlap between the upstream anchor and the intermediate portion of the implantable device; and a second folded portion between the downstream anchor of the implantable device and the intermediate portion of the implantable device, such that along a longitudinal direction of the implantable device, there is partial overlap between the downstream anchor and the intermediate portion of the implantable device.

Inventive concept 6. The apparatus according to any one of inventive concepts 2-5, wherein the implantable device is configured such that the proximal end of the conduit is disposed eccentrically with respect to the upstream anchor.

Inventive concept 7. The apparatus according to any one of inventive concepts 2-5, wherein the intermediate portion of the implantable device comprises a frame, and wherein the intermediate portion is configured to define the curved longitudinal axis at least partially by virtue of the frame being cut such that a side of the frame that is configured to be placed on the inside of the curve of the aorta is shorter than the side of the frame that is configured to be placed on the outside of the curve.

Inventive concept 8. The apparatus according to any one of inventive concepts 2-5, wherein the intermediate portion of the implantable device comprises a frame that comprises a spiraling set of struts.

Inventive concept 9. The apparatus according to any one of inventive concepts 2-5, wherein the upstream anchor comprises a flared skirt at an upstream end of the upstream anchor, the flared skirt being configured to become deployed within aortic sinuses of the subject, and to exert an outward normal force upon an inner wall of the aortic sinuses.

Inventive concept 10. The apparatus according to any one of inventive concepts 2-5, wherein the upstream anchor comprises a plurality of anchors at an upstream end of the upstream anchor, the anchors being configured to become deployed within respective aortic sinuses of the subject, and to exert an outward normal force upon an inner wall of the aortic sinuses.

Inventive concept 11. The apparatus according to any one of inventive concepts 2-5, wherein the intermediate portion comprises one or more centralizing anchors extending radially therefrom, the centralizing anchors being configured to at least partially centralize the conduit with respect to a longitudinal axis of the aorta.

For some applications, the apparatus and methods described herein are combined with apparatus and methods described in the following applications, all of which are incorporated herein by reference:

International Patent Application WO 18/029688, filed Aug. 10, 2017, which claims priority from U.S. Provisional Application 62/373,993 to Karavany, filed Aug. 12, 2016, entitled "Aortic implant."

US 2018/0036109, which is the U.S. national phase of WO 16/128983, and which claims priority from:

U.S. Provisional Application 62/115,207 to Karavany, filed Feb. 12, 2015, entitled "Aortic implant," and U.S. Provisional Application 62/265,571 to Karavany, filed Dec. 10, 2015, entitled "Aortic implant."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:

implanting an aortic pressure-loss-reduction device in an ascending aorta of a subject, the aortic pressure-loss-reduction device including a frame and a material that is configured to impede blood flow therethrough coupled to at least a portion of the frame, by, sequentially:

while the aortic pressure-loss-reduction device is inside a catheter, placing a distal end of the catheter within the subject's ascending aorta, the aortic pressure-loss-reduction device being disposed within the catheter such the device is maintained in a radially-constrained configuration and such that an upstream anchor of the device is disposed distally within the catheter with respect to a downstream anchor of the device;

retracting a proximal covering sheath of the catheter, such as to:

uncover an intermediate portion of the aortic pressure-loss-reduction device to allow the intermediate portion to at least partially assume its non-constrained configuration, the intermediate portion of the device being configured to define a conduit through the device; and uncover a portion of the downstream anchor, such that the uncovered portion of the downstream anchor includes a portion of the frame that does not have the material coupled thereto, while maintaining the downstream anchor in an at least partially-radially-constrained state;

advancing a distal covering sheath of the catheter, such as to cause the upstream anchor to anchor an upstream end of the aortic pressure-loss-reduction device to the subject's ascending aorta, by the upstream anchor radially expanding against an inner wall of the ascending aorta, the upstream anchor being having material coupled thereto, such that blood flows from the aortic valve into an upstream end of the device and out of the uncovered portion of the downstream anchor; and further retracting the proximal covering sheath of the catheter, such as to cause the downstream anchor to anchor a downstream end of the aortic pressure-loss-reduction device to the subject's ascending aorta, by the downstream anchor radially expanding against an inner wall of the ascending aorta.

2. The method according to claim 1, further comprising, while retracting the proximal covering sheath of the catheter, preventing the upstream anchor from radially expanding by holding projections that protrude from an upstream end of the upstream anchor within the distal covering sheath of the catheter.

3. The method according to claim 1, wherein retracting the proximal covering sheath of the catheter such as to uncover the portion of the downstream anchor that does not have the material coupled to it comprises facilitating blood flow through the device by allowing blood to flow through the portion of the downstream anchor that does not have the material coupled thereto.

4. The method according to claim 1, wherein causing the downstream anchor to anchor a downstream end of the device to the subject's ascending aorta, by the downstream anchor radially expanding against an inner wall of the ascending aorta comprises preventing blood flow to a brachiocephalic artery of the subject from being occluded by deploying the downstream anchor such that the portion of the frame that does not have the material coupled to it is deployed closest to the brachiocephalic artery.

5. The method according to claim 1, wherein while the device is inside the catheter at least a portion of the device is disposed around a conically-shaped mount portion that converges toward a proximal end of the catheter, the method further comprising, subsequent to further retracting the proximal covering sheath of the catheter such as to cause the downstream anchor to anchor a downstream end of the device to the subject's ascending aorta, retracting the mount portion through the conduit, the conical shape of the mount portion being configured to facilitate retraction of the mount through the conduit.

6. The method according to claim 1, wherein implanting the aortic pressure-loss-reduction device in the subject's ascending aorta comprises implanting the aortic pressure-loss-reduction device in the subject's ascending aorta such that an upstream end of the conduit is disposed within 25 mm of an aortic valve orifice of the subject.

7. The method according to claim 1, wherein advancing the distal covering sheath of the catheter, such as to cause the upstream anchor to anchor the upstream end of the device to the subject's ascending aorta, by the upstream anchor radially expanding against an inner wall of the ascending aorta comprises causing the upstream end of the upstream anchor to become deployed within 5 mm of a sinotubular junction of the subject.

8. The method according to claim 7, wherein causing the upstream end of the upstream anchor to become deployed within 5 mm of the subject's sinotubular junction comprises causing the upstream end of the upstream anchor to become deployed within 5 mm of the subject's sinotubular junction, upstream of the subject's sinotubular junction.

9. The method according to claim 7, wherein causing the upstream end of the upstream anchor to become deployed within 5 mm of the subject's sinotubular junction comprises causing the upstream end of the upstream anchor to become deployed within 5 mm of the subject's sinotubular junction, downstream of the subject's sinotubular junction.

10. An apparatus comprising:

an aortic pressure-loss-reduction device configured to be implanted in an ascending aorta of a subject, the aortic pressure-loss-reduction device comprising a frame, and a material that is configured to impede blood flow therethrough coupled to at least a portion of the frame, the aortic pressure-loss-reduction device being configured such that in a non-radially-constrained configuration of the device, the device defines:

an upstream anchor, a downstream anchor, at least a portion of the downstream anchor being defined by the frame and not including any material coupled to the frame, and an intermediate portion of the device that defines a conduit through the aortic pressure-loss-reduction device; and a catheter configured to be inserted into the subject's ascending aorta, while housing the aortic pressure-loss-reduction device inside the catheter in a radially constrained configuration, with the upstream anchor disposed within the catheter distally with respect to the downstream anchor, the catheter comprising:

a proximal covering sheath configured to be retracted such as to sequentially:

uncover the intermediate portion of the aortic pressure-loss-reduction device to allow the intermediate portion to at least partially assume its non-constrained configuration, and uncover a portion of the downstream anchor, such that the uncovered portion of the downstream anchor includes the portion of the frame that does not have the material coupled thereto, while maintaining the downstream anchor in an at least partially-radially-constrained state;

a distal covering sheath of the catheter configured, subsequent to the proximal covering sheath being retracted such as to uncover at least the portion of the downstream anchor, to be advanced distally as to cause the upstream anchor to anchor an upstream end of the aortic pressure-loss-reduction device to the subject's ascending aorta, by the upstream anchor radially expanding against an inner wall of the ascending aorta, the upstream anchor having material covered thereto, such that blood flows from the aortic valve into an upstream end of the device and out of the uncovered portion of the downstream anchor;

the proximal covering sheath being further configured, subsequent to the distal covering sheath being advanced distally, to be further retracted, such as to cause the downstream anchor to anchor a downstream end of the aortic pressure-loss-reduction device to the subject's ascending aorta, by the downstream anchor radially expanding against the inner wall of the ascending aorta.

11. The apparatus according to claim 10, wherein the catheter further comprises a mount, at least a distal portion of which defines a conical shape that converges toward a proximal end of the catheter, the distal portion of the mount being configured such that:
   while the device is inside the catheter at least a portion of the device is disposed around the distal portion of the mount, and
   the conical shape of the distal portion of the mount is configured to facilitate retraction of the distal portion of the mount through the conduit.

12. The apparatus according to claim 10, wherein the aortic pressure-loss-reduction device is configured to be implanted in the subject's ascending aorta such that an upstream end of the conduit is disposed within 25 mm of an aortic valve orifice of the subject.

13. The apparatus according to claim 10, wherein the aortic pressure-loss-reduction device is configured to be implanted in the subject's ascending aorta such that an upstream end of the upstream anchor is deployed within 5 mm of a sinotubular junction of the subject.

14. The apparatus according to claim 13, wherein the aortic pressure-loss-reduction device is configured to be implanted in the subject's ascending aorta such that the upstream end of the upstream anchor is deployed within 5 mm of the subject's sinotubular junction, upstream of the subject's sinotubular junction.

15. The apparatus according to claim 13, wherein the aortic pressure-loss-reduction device is configured to be implanted in the subject's ascending aorta such that the upstream end of the upstream anchor is deployed within 5 mm of the subject's sinotubular junction, downstream of the subject's sinotubular junction.

16. The apparatus according to claim 10, wherein the aortic pressure-loss-reduction device further comprises a plurality of projections that protrude from an upstream end of the upstream anchor, and wherein the distal covering sheath of the catheter is configured to prevent the upstream anchor from radially expanding by holding the projections.

17. The apparatus according to claim 16, wherein the projections comprises T-shaped projections.

18. The apparatus according to claim 16, wherein the projections each have lengths of less than 8 mm.

19. The apparatus according to claim 16, wherein upstream ends of the projections are curved such as to be atraumatic.

20. A method comprising:
   placing an aortic pressure-loss-reduction device inside an ascending aorta of a subject, the aortic pressure-loss-reduction device including a frame and a material layer coupled to an inside of at least a portion of the frame, the material being configured to impede blood flow therethrough; and
   deploying the aortic pressure-loss-reduction device inside the ascending aorta, such that the frame of the aortic pressure-loss-reduction device defines:
      an upstream anchor portion that radially expands against an inner wall of a subject's ascending aorta, such as to anchor an upstream end of the aortic pressure-loss-reduction device to the subject's ascending aorta,
      an intermediate portion that defines a conduit therethrough, such that blood flows through the device via the conduit, at least a portion of the conduit diverging, such that a downstream end of the diverging portion has a greater cross-sectional area than an upstream end of the diverging portion,
      a downstream anchor portion that radially expands against an inner wall of a subject's ascending aorta, such as to anchor a downstream end of the aortic pressure-loss-reduction device to the subject's ascending aorta,
      a first set of sinusoidal struts disposed between a downstream end of the upstream anchor and an upstream end of the intermediate portion, the sinusoidal struts forming a folded portion between the downstream end of the upstream anchor and the upstream end of the intermediate portion, and
      an upstream end of the intermediate portion being reinforced with respect to at least a central portion of the intermediate portion, such that in response to a diameter of the upstream anchor changing by an absolute amount, an absolute change in a diameter of the upstream end of the intermediate portion is less than the absolute amount by which the diameter of the upstream anchor changes.

* * * * *